United States Patent
Iwadate et al.

(10) Patent No.: US 7,521,043 B2
(45) Date of Patent: Apr. 21, 2009

(54) GENE THERAPY FOR TUMORS USING MINUS-STRAND RNA VIRAL VECTORS ENCODING IMMUNOSTIMULATORY CYTOKINES

(75) Inventors: Yasuo Iwadate, Chiba (JP); Akira Yamaura, Chiba (JP); Makoto Inoue, Ibaraki (JP); Mamoru Hasegawa, Ibaraki (JP)

(73) Assignee: DNAVEC Research Inc., Ibaraki (JP)

( * ) Notice: Subject to any disclaimer, the term of this patent is extended or adjusted under 35 U.S.C. 154(b) by 0 days.

(21) Appl. No.: 10/585,884

(22) PCT Filed: Jan. 12, 2005

(86) PCT No.: PCT/JP2005/000238

§ 371 (c)(1),
(2), (4) Date: Nov. 20, 2006

(87) PCT Pub. No.: WO2005/067981

PCT Pub. Date: Jul. 28, 2005

(65) Prior Publication Data

US 2007/0248627 A1    Oct. 25, 2007

(30) Foreign Application Priority Data

Jan. 13, 2004    (JP)    ............... 2004-005186

(51) Int. Cl.
*A01N 63/00* (2006.01)
*A01N 43/04* (2006.01)
(52) U.S. Cl. ........................ 424/93.2; 514/44
(58) Field of Classification Search ............... 424/93.2, 424/93.21; 514/44
See application file for complete search history.

(56) References Cited

U.S. PATENT DOCUMENTS

| 6,514,728 | B1* | 2/2003 | Kai et al. .................... 435/69.5 |
| 6,645,760 | B2 | 11/2003 | Nagai et al. |
| 6,723,532 | B2 | 4/2004 | Nagai et al. |
| 7,101,685 | B2 | 9/2006 | Nagai et al. |
| 2002/0012995 | A1 | 1/2002 | Fukumura et al. |
| 2002/0169306 | A1 | 11/2002 | Kitazato et al. |
| 2003/0022376 | A1 | 1/2003 | Kitazato et al. |
| 2003/0166252 | A1 | 9/2003 | Kitazato et al. |
| 2003/0170266 | A1 | 9/2003 | Kitazato et al. |
| 2004/0053877 | A1 | 3/2004 | Fukumura et al. |
| 2004/0101965 | A1 | 5/2004 | Griesenbach et al. |
| 2004/0265272 | A1 | 12/2004 | Iwamoto et al. |
| 2005/0130123 | A1 | 6/2005 | Inoue et al. |
| 2005/0158279 | A1 | 7/2005 | Fukumura et al. |
| 2005/0191617 | A1 | 9/2005 | Inoue et al. |
| 2005/0266566 | A1 | 12/2005 | Nagai et al. |
| 2005/0271628 | A1 | 12/2005 | Fukumura et al. |
| 2006/0104950 | A1 | 5/2006 | Okano et al. |
| 2006/0128019 | A1 | 6/2006 | Kobayashi et al. |
| 2007/0009949 | A1 | 1/2007 | Kitazato et al. |
| 2007/0269414 | A1 | 11/2007 | Okano et al. |
| 2008/0014183 | A1 | 1/2008 | Okano et al. |
| 2008/0031855 | A1 | 2/2008 | Okano et al. |

FOREIGN PATENT DOCUMENTS

| EP | 0 864 645 A1 | 9/1998 |
| JP | 58-157723 A | 9/1983 |
| JP | 7-503455 A | 4/1995 |
| JP | 2000-253876 | 9/2000 |
| WO | WO 97/16539 A1 | 5/1997 |
| WO | WO 00/01837 A1 | 1/2000 |
| WO | WO 00/70055 A1 | 11/2000 |
| WO | WO 00/70070 A1 | 11/2000 |
| WO | WO 01/04271 A2 | 1/2001 |
| WO | WO 02/31138 A1 | 4/2002 |
| WO | WO 02/38726 A2 | 5/2002 |
| WO | WO 03/025570 A1 | 3/2003 |
| WO | WO 03/029475 A1 | 4/2003 |
| WO | WO 03/102183 A1 | 12/2003 |
| WO | WO 2004/022731 A1 | 3/2004 |
| WO | WO 2004/038029 A1 | 5/2004 |

OTHER PUBLICATIONS

Bitzer (J. Gene Med., 2003, vol. 5, p. 543-553).*
Bitzer et al., "Sendai Virus Vectors as an Emerging Negative-Strand RNA Viral Vector System," *J. Gen. Med.* 5(7):543-553 (2003).
Bitzer et al., "Negative-strand RNA Viral Vectors: Intravenous Application of Sendai Virus Vectors for the Systemic Delivery of Therapeutic Genes," *Mol. Ther.* 7(2): 210-217 (2003).

(Continued)

*Primary Examiner*—Michael C. Wilson
(74) *Attorney, Agent, or Firm*—Clark & Elbing LLP

(57) ABSTRACT

The present invention provides methods for treating tumors, which comprise the step of administering into tumor sites a minus-strand RNA viral vector encoding an immunostimulatory cytokine or cells introduced with the vector. The present invention also provides compositions for treating tumors, which comprise as an active ingredient the minus-strand RNA viral vector encoding an immunostimulatory cytokine or cells introduced with the vector. The present invention also provides kits for treating tumors, which comprise the minus-strand RNA viral vector encoding an immunostimulatory cytokine, and a tumor antigen or a vector expressing the antigen.

4 Claims, 7 Drawing Sheets

OTHER PUBLICATIONS

Boviatsis et al., "Gene Transfer into Experimental Brain Tumors Mediated by Adenovirus, Herpes Simplex Virus, and Retrovirus Vectors," *Hum. Gene Ther.* 5(2): 183-191 (1994).

Giezeman-Smits et al., "Cytokine Gene Therapy of Gliomas: Induction of Reactive CD4+ T Cells by Interleukin-4-Transfected 9L Gliosarcoma Is Essential for Protective Immunity," *Cancer Res.* 60(9): 2449-2457 (2000).

Hasegawa, "Shinki Idenshi Chiryoyo Vector No Kaihatsu," *The Cell (Saibou)* 33(6): 227-231 (2001).

Herrlinger et al., "Vaccination for Experimental Gliomas using GM-CSF-Transduced Glioma Cells," *Cancer Gene Ther.* 4(6): 345-352 (1997).

Inoue et al., "Matrix and Fusion Genes-Deficient Sendai Virus Vector: Efficient Gene Transfer with Preferable Properties," *Mol. Ther.* 5(5): S174-S175, Abstract #530 (2002).

Inoue et al., "Recombinant Sendai Virus Vectors Deleted in both the Matrix and the Fusion Genes: Efficient Gene Transfer with Preferable Properties," *J. Gene Med.* 6(10): 1069-1081 (2004).

Iwadate et al., "Induction of Acquired Immunity in Rats that have Eliminated Intracranial Gliosarcoma Cells by the Expression of Herpes Simplex Virus-Thymidine Kinase Gene and Ganciclovir Administration," *Oncology* 54(4): 329-334 (1997).

Iwadate et al., "Immunological Responsiveness to Interleukin-2-Producing Brain Tumors can be Restored by Concurrent Subcutaneous Transplantation of the Same Tumors," *Cancer Gene Ther.* 7(9): 1263-1269 (2000).

Iwadate et al., "Induction of Immunity in Peripheral Tissues Combined with Intracerebral Transplantation of Interleukin-2-Producing Cells Eliminates Established Brain Tumors," *Cancer Res.* 61(24): 8769-8774 (2001).

Iwadate et al., "Interleukin-12-Mediated Induction of Systemic Immunity in the Periphery and Recruitment of Activated T Cells into the Brain Produce Limited Antitumor Effects Compared with Interleukin-2," *Int. J. Mol. Med.* 10(6): 741-747 (2002).

Iwadate et al., "Glioma-Specific Cytotoxic T Cells can be Effectively Induced by Subcutaneous Vaccination of Irradiated Wild-Type Tumor Cells without Artificial Cytokine Production," *Int. J. Oncol.* 23(2): 483-488 (2003).

Kramm et al., "Therapeutic Efficiency and Safety of a Second-Generation Replication-Conditional HSV1 Vector for Brain Tumor Gene Therapy," *Hum. Gene Ther.* 8(17): 2057-2068 (1997).

Li et al., "A Cytoplasmic RNA Vector Derived from Nontransmissible Sendai Virus with Efficient Gene Transfer and Expression," *J. Virol.* 74(14): 6564-6569 (2000).

Ram et al., "In Situ Retroviral-Mediated Gene Transfer for the Treatment of Brain Tumors in Rats," *Cancer Res.* 53(1): 83-88 (1993).

Ram et al., "In Vivo Transfer of the Human Interleukin-2 Gene: Negative Tumoricidal Results in Experimental Brain Tumors," *J. Neurosurg.* 80(3): 535-540 (1994).

Ram et al., "Therapy of Malignant Brain Tumors by Intratumoral Implantation of Retroviral Vector-Producing Cells," *Nat. Med.* 3(12): 1354-1361 (1997).

Saleh et al., "Effect of In Situ Retroviral Interleukin-4 Transfer on Established Intracranial Tumors," *J. Natl. Cancer Inst.* 91(5): 438-445 (1999).

Sampson et al., "Subcutaneous Vaccination with Irradiated, Cytokine-Producing Tumor Cells Stimulates CD8+ Cell-Mediated Immunity Against Tumors Located in the "Immunologically Privileged" Central Nervous System," *Proc. Natl. Acad. Sci. U.S.A.* 93(19): 10399-10404 (1996).

Shapiro, "Current Therapy for Brain Tumors," *Arch. Neurol.* 56(4): 429-432 (1999).

Shirakura et al., "Sendai Virus Vector-Mediated Gene Transfer of Glial Cell Line-Derived Neurotrophic Factor Prevents Delayed Neuronal Death after Transient Global Ischemia in Gerbils," *Exp. Anim.* 52(2): 119-127 (2003).

Suzuki et al., "Feeding Suppression by Fibroblast Growth Factor-1 is Accompanied by Selective Induction of Heat Shock Protein 27 in Hypothalamic Astrocytes," *Eur. J. Neurosci.* 13(12): 2299-2308 (2001).

Inoue et al., "A New Sendai Virus Vector Deficient in the Matrix Gene Does Not Form Virus Particles and Shows Extensive Cell-to-Cell Spreading," *Journal of Virology* 77(11):6419-6429 (2003).

Iwadate et al., "Recombinant Sendai Virus Vector Induces Complete Remission of Established Brain Tumors through Efficient Interleukin-2 Gene Transfer in Vaccinated Rats," *Clin. Cancer Res.* 11(10):3821-3827 (2005).

Markwell et al., "Specific Gangliosides Function as Host Cell Receptors for Sendai Virus," *Proc. Natl. Acad. Sci. USA* 78(9):5406-5410 (1981).

Li et al., "A Cytoplasmic RNA Vector Derived from Nontransmissable Sendai Virus with Efficient Gene Transfer and Expression" *J. Virol.* 74(14):6564-6569 (2000).

Shirakura et al., "Sendai Virus Vector-mediated Gene Transfer of Glial Cell Line-Derived Neurotrophic Factor Prevents Delayed Neuronal Death After Transient Global Ischemia in Gerbils," *Exp. Anim.* 52(2):119-127 (2003).

Suzuki et al., "Feeding Suppression by Fibroblast Growth Factor-1 Is Accompanied by Selective Induction of Heat Shock Protein 27 in Hypothalamic Astrocytes," *Eur. J. Neurosci.* 13:2299-2308 (2001).

International Search Report for PCT/JP2005/000238, mailed Apr. 26, 2005.

Supplemental European Search Report for EP 05 70 3477, dated Mar. 1, 2007.

Crystal, "Transfer of Genes to Humans: Early Lessons and Obstacles to Success," *Science*, 270: 404-410, 1995.

Deonarain, "Ligand-targeted Receptor-mediated Vectors for Gene Delivery" *Expert Opinion on Therapeutic Patents*, 8: 53-69, 1998.

Miller et al., "Targeted Vectors for Gene Therapy," *The FASEB Journal*, 9: 190-199, 1995.

Ross et al., "Gene Therapy in the United States: a Five-year Status Report," *Hum Gene Ther.*, 7: 1781-1790, 1996.

Verma et al., "Gene Therapy - Promises, Problems and Prospects" *Nature* 389, 239-242, 1997.

* cited by examiner

NORMAL BRAIN
TISSUE

BRAIN TUMOR

DAY 4   DAY 7   DAY 14

SEQUENCE LISTING

```
<160> NUMBER OF SEQ ID NOS: 20

<210> SEQ ID NO 1
<211> LENGTH: 399
<212> TYPE: DNA
<213> ORGANISM: Homo sapiens
<220> FEATURE:
<221> NAME/KEY: CDS
<222> LOCATION: (1)..(399)

<400> SEQUENCE: 1 gca cct act tca agt tct aca aag aaa aca cag cta caa ctg gag cat        48
Ala Pro Thr Ser Ser Ser Thr Lys Lys Thr Gln Leu Gln Leu Glu His
1               5                   10                  15 tta ctg ctg gat tta cag atg att ttg aat gga att aat aat tac aag        96
Leu Leu Leu Asp Leu Gln Met Ile Leu Asn Gly Ile Asn Asn Tyr Lys
                20                  25                  30 aat ccc aaa ctc acc agg atg ctc aca ttt aag ttt tac atg ccc aag       144
Asn Pro Lys Leu Thr Arg Met Leu Thr Phe Lys Phe Tyr Met Pro Lys
            35                  40                  45 aag gcc aca gaa ctg aaa cat ctt cag tgt cta gaa gaa gaa ctc aaa       192
Lys Ala Thr Glu Leu Lys His Leu Gln Cys Leu Glu Glu Glu Leu Lys
        50                  55                  60 cct ctg gag gaa gtg cta aat tta gct caa agc aaa aac ttt cac tta       240
Pro Leu Glu Glu Val Leu Asn Leu Ala Gln Ser Lys Asn Phe His Leu
65                  70                  75                  80 aga ccc agg gac tta atc agc aat atc aac gta ata gtt ctg gaa cta       288
Arg Pro Arg Asp Leu Ile Ser Asn Ile Asn Val Ile Val Leu Glu Leu
                85                  90                  95 aag gga tct gaa aca aca ttc atg tgt gaa tat gct gat gag aca gca       336
Lys Gly Ser Glu Thr Thr Phe Met Cys Glu Tyr Ala Asp Glu Thr Ala
            100                 105                 110 acc att gta gaa ttt ctg aac aga tgg att acc ttt tgt caa agc atc       384
Thr Ile Val Glu Phe Leu Asn Arg Trp Ile Thr Phe Cys Gln Ser Ile
        115                 120                 125 atc tca aca ctg act                                                    399
Ile Ser Thr Leu Thr
    130

<210> SEQ ID NO 2
<211> LENGTH: 133
```

```
<212> TYPE: PRT
<213> ORGANISM: Homo sapiens

<400> SEQUENCE: 2

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
            115                 120                 125

Ile Ser Thr Leu Thr
        130

<210> SEQ ID NO 3
<211> LENGTH: 10
<212> TYPE: RNA
<213> ORGANISM: Artificial
<220> FEATURE:
<223> OTHER INFORMATION: an example of S sequence of Sendai Virus

<400> SEQUENCE: 3 ucccwvuuwc                                                                10

<210> SEQ ID NO 4
<211> LENGTH: 10
<212> TYPE: RNA
<213> ORGANISM: Artificial
<220> FEATURE:
<223> OTHER INFORMATION: an example of S sequence of Sendai Virus

<400> SEQUENCE: 4
ucccaguuuc                                                                10

<210> SEQ ID NO 5
<211> LENGTH: 10
<212> TYPE: RNA
<213> ORGANISM: Artificial
<220> FEATURE:
<223> OTHER INFORMATION: an example of S sequence of Sendai Virus

<400> SEQUENCE: 5
ucccacuuac                                                                10

<210> SEQ ID NO 6
<211> LENGTH: 10
<212> TYPE: RNA
<213> ORGANISM: Artificial
<220> FEATURE:
<223> OTHER INFORMATION: an example of S sequence of Sendai Virus

<400> SEQUENCE: 6
ucccacuuuc                                                                10
```

```
<210> SEQ ID NO 7
<211> LENGTH: 10
<212> TYPE: DNA
<213> ORGANISM: Artificial
<220> FEATURE:
<223> OTHER INFORMATION: an example of S sequence of Sendai Virus

<400> SEQUENCE: 7
agggtcaaag                                                           10

<210> SEQ ID NO 8
<211> LENGTH: 10
<212> TYPE: DNA
<213> ORGANISM: Artificial
<220> FEATURE:
<223> OTHER INFORMATION: an example of S sequence of Sendai Virus

<400> SEQUENCE: 8
agggtgaatg                                                           10

<210> SEQ ID NO 9
<211> LENGTH: 10
<212> TYPE: DNA
<213> ORGANISM: Artificial
<220> FEATURE:
<223> OTHER INFORMATION: an example of S sequence of Sendai Virus

<400> SEQUENCE: 9
agggtgaaag                                                           10

<210> SEQ ID NO 10
<211> LENGTH: 9
<212> TYPE: RNA
<213> ORGANISM: Artificial
<220> FEATURE:
<223> OTHER INFORMATION: an example of E sequence of Sendai Virus

<400> SEQUENCE: 10 auucuuuuu                                                             9

<210> SEQ ID NO 11
<211> LENGTH: 9
<212> TYPE: DNA
<213> ORGANISM: Artificial
<220> FEATURE:
<223> OTHER INFORMATION: an example of E sequence of Sendai Virus

<400> SEQUENCE: 11 taagaaaaa                                                             9

<210> SEQ ID NO 12
<211> LENGTH: 10
<212> TYPE: DNA
<213> ORGANISM: Artificial
<220> FEATURE:
<223> OTHER INFORMATION: an example of S sequence of Sendai Virus

<400> SEQUENCE: 12
ctttcaccct                                                           10

<210> SEQ ID NO 13
<211> LENGTH: 15
<212> TYPE: DNA
<213> ORGANISM: Artificial
<220> FEATURE:
```

<223> OTHER INFORMATION: an example of E sequence of Sendai Virus

<400> SEQUENCE: 13
tttttcttac tacgg                                                           15

<210> SEQ ID NO 14
<211> LENGTH: 18
<212> TYPE: DNA
<213> ORGANISM: Artificial
<220> FEATURE:
<223> OTHER INFORMATION: an artificially synthesized linker sequence

<400> SEQUENCE: 14
atgcatgccg gcagatga                                                        18

<210> SEQ ID NO 15
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 15
gttgagtact gcaagagc                                                        18

<210> SEQ ID NO 16
<211> LENGTH: 42
<212> TYPE: DNA
<213> ORGANISM: Artificial
<220> FEATURE:
<223> OTHER INFORMATION: an artificially synthesized primer sequence

<400> SEQUENCE: 16
tttgccggca tgcatgtttc ccaaggggag agttttgcaa cc                              42

<210> SEQ ID NO 17
<211> LENGTH: 18
<212> TYPE: DNA
<213> ORGANISM: Artificial
<220> FEATURE:
<223> OTHER INFORMATION: an artificially synthesized primer sequence

<400> SEQUENCE: 17
atgcatgccg gcagatga                                                        18

<210> SEQ ID NO 18
<211> LENGTH: 21
<212> TYPE: DNA
<213> ORGANISM: Artificial
<220> FEATURE:
<223> OTHER INFORMATION: an artificially synthesized primer sequence

<400> SEQUENCE: 18
tgggtgaatg agagaatcag c                                                    21

<210> SEQ ID NO 19
<211> LENGTH: 51
<212> TYPE: DNA
<213> ORGANISM: Artificial
<220> FEATURE:
<223> OTHER INFORMATION: an artificially synthesized primer sequence

<400> SEQUENCE: 19
acttgcggcc gcgtttaaac ggcgcgccat gtacaggatg caactcctgt c                   51

-continued

```
<210> SEQ ID NO 20
<211> LENGTH: 63
<212> TYPE: DNA
<213> ORGANISM: Artificial
<220> FEATURE:
<223> OTHER INFORMATION: an artificially synthesized primer sequence

<400> SEQUENCE: 20
atccgcggcc gcgatgaact ttcaccctaa gttttctta ctacggattt aaatggcgcg      60
cca                                                                  63
```

GENE THERAPY FOR TUMORS USING MINUS-STRAND RNA VIRAL VECTORS ENCODING IMMUNOSTIMULATORY CYTOKINES

CROSS-REFERENCE TO RELATED APPLICATIONS

This application is the U.S. National Stage of International Application No. PCT/JP2005/000238, filed Jan. 12, 2005, which, in turn, claims the benefit of Japanese Patent Application No. 2004-005186, filed Jan. 13, 2004.

TECHNICAL FIELD

The present invention relates to tumor gene therapy using minus-strand RNA viral vectors that encode immunostimulatory cytokines.

BACKGROUND ART

In recent years, cancer immunotherapy using cytokines has received attention. For example, therapeutic strategies using gene introduction have been explored for treatment of glioblastoma (Glioblastoma multiforme; GBM) (Shapiro, W. R., Arch. Neurol., 56: 429-432, 1999), which is one of the malignant brain tumors that has been thought to be untreatable in spite of various approaches including surgery, radiotherapy, and chemotherapy (Ram, Z. et al., Cancer Res., 53: 83-88, 1993; Sampson, J. H. et al., Proc. Natl. Acad. Sci. USA, 93: 10399-10404, 1996; Herrlinger, U. et al., Cancer Gene Ther., 4: 345-352, 1997; Seleh, M. et al., J. Natl. Cancer Inst., 91: 438-445, 1999; Giezeman-Smits, K. M. et al., Cancer Res., 60: 2449-2457, 2000). Some gene therapy strategies are expected to be effective based on in vivo animal model studies. However, low gene introduction efficiency limits their therapeutic effects in almost all cases. Major obstacles to a successful use of such gene therapy strategies are inability of recombinant viral vectors to spread to the whole tumor mass and low efficiency of in vivo introduction (Ram, Z. et al., Nat. Med., 3: 1354-1361, 1997). To promote gene therapy, development of a new vector system that is capable of safely and efficiently introducing genes into target cells is needed.

Non-patent Document 1: Shapiro, W. R., Arch. Neurol., 56: 429-432, 1999
Non-patent Document 2: Ram, Z. et al., Cancer Res., 53: 83-88, 1993
Non-patent Document 3: Sampson, J. H. et al., Proc. Natl. Acad. Sci. USA, 93: 10399-10404, 1996
Non-patent Document 4: Herrlinger, U. et al., Cancer Gene Ther., 4: 345-352, 1997
Non-patent Document 5: Seleh, M. et al., J. Natl. Cancer Inst., 91: 438-445, 1999
Non-patent Document 6: Giezeman-Smits, K. M. et al., Cancer Res., 60: 2449-2457, 2000
Non-patent Document 7: Ram, Z. et al., Nat. Med., 3: 1354-1361, 1997

DISCLOSURE OF THE INVENTION

Problems to Be Solved by the Invention

An objective of the present invention is to provide methods for treating tumors using minus-strand RNA viral vectors that encode immunostimulatory cytokines. Another objective of the present invention is to provide compositions and kits for treating tumors which comprise minus-strand RNA viral vectors encoding immunostimulatory cytokines, and methods for producing them.

Means to Solve the Problems

The minus-strand RNA virus is an envelope virus that carries minus-strand RNA (also referred to as negative strand RNA) as genome. The virus exhibits high infectivity and is capable of expressing genes that it carries at high levels in the cytoplasm. In recent years, the advance in handling minus-strand RNA viral genome has enabled additional insertion of non-viral genes into the viral genome and thus the development of a new class of viral vectors for gene introduction approaches (Bitzer, M. et al., J. Gene Med., 5: 543-553, 2003).

The replication cycle of minus-strand RNA virus occurs in the cytoplasm without integration into the genome DNA of infected cells. Thus, this ensures safety in clinical applications of gene therapy, and the virus is thought to be useful as a tool for producing therapeutic recombinant proteins by cell culture, or for producing secretory proteins suitable for application in immunogene therapy that uses cytokines or chemokines. The minus-strand RNA virus has advantages such as: (i) there is no risk of integration into genome DNA because the replication cycle occurs exclusively in the cytoplasm; (ii) the introduction efficiency does not depend on the cell cycle of target cells; (iii) homologous recombination does not take place between the virus and a different viral genome or the wild type virus; (iv) virus incorporation into cells requires only a very short contact time; (v) genes encoded by the virus can be strongly expressed in a broad range of host cells with adjustability.

To test the therapeutic potential of the tumor gene therapy strategy that uses minus-strand RNA viral vectors for introducing cytokine genes, the present inventors introduced into tumors SeV vectors that carry immunostimulatory cytokine genes and evaluated their anti-tumor effects. An SeV carrying the interleukin-2 (IL-2) gene, which is an immunostimulatory cytokine, was constructed. The SeV vector was administered intracerebrally (I.C.) into a brain tumor model rat. As a result, it was found that the introduction of the cytokine gene into tumors by SeV resulted in significant suppression of tumor growth. Moreover, when the IL-2-expressing SeV vector was injected into an established brain tumor after peripheral vaccination with irradiated wild-type 9L cells, it was revealed that tumor growth was drastically reduced and the brain tumors were eliminated in three of the ten rats tested. Immunohistochemical analyses revealed that high levels of CD4[+] and CD8[+] T cells infiltrated into brain tumors that were treated with the IL-2-expressing SeV vector. It was thus discovered that the SeV vector-mediated gene introduction into tumors produces significant therapeutic effects. The introduction of immunostimulatory cytokine-encoding minus-strand RNA viral vectors into tumors is expected to become a new gene therapy strategy against tumors.

Specifically, the present invention relates to methods for treating tumors using minus-strand RNA viral vectors that encode immunostimulatory cytokines, and compositions and kits for treating tumors comprising minus-strand RNA viral vectors that encode immunostimulatory cytokines, and such. More specifically, the present invention relates to the invention of each of the claims. The present invention also relates to inventions comprising a desired combination of one or more (or all) inventions set forth in the claims, in particular, to inventions comprising a desired combination of one or more (or all) inventions set forth in the claims (dependent claims) that cite the same independent claim(s) (claim(s) relating to inventions not encompassed by inventions recited in other claims). An invention set forth in each independent claim is also intended to include any combinations of the inventions set forth in its dependent claims. Specifically, the present invention includes:

[1] a method of anti-tumor treatment comprising the step of administering a minus-strand RNA viral vector encoding an immunostimulatory cytokine or a cell into which the vector has been introduced;

[2] the method of [1] further comprising the step of immunizing with a tumor antigen or a vector expressing the antigen;

[3] the method of [2], wherein the immunization is achieved by subcutaneously inoculating the tumor antigen or the antigen-expressing vector;

[4] the method of [2] or [3], wherein the tumor antigen is a tumor cell that has lost growth ability or a tumor cell lysate;

[5] the method of any one of [1] to [4], wherein the tumor is a brain tumor;

[6] the method of any one of [1] to [5], wherein the immunostimulatory cytokine is interleukin-2;

[7] an anti-tumor composition which comprises as an active ingredient a minus-strand RNA viral vector encoding an immunostimulatory cytokine or a cell introduced with the vector;

[8] the composition of [7], wherein the immunostimulatory cytokine is interleukin-2;

[9] an anti-tumor treatment kit comprising: (a) a minus-strand RNA viral vector encoding an immunostimulatory cytokine and (b) a tumor antigen or a vector expressing the antigen; and

[10] the kit of [9], wherein the immunostimulatory cytokine is interleukin-2.

The present invention demonstrates that the minus-strand RNA viral vector efficiently delivered immunostimulatory cytokine genes into intracerebral tumors. The present invention also demonstrates that the i.c. administration of an immunostimulatory cytokine-encoding minus-strand RNA viral vector could produce marked anti-glioma effects and, in particular, completely eliminated established brain tumors when combined with tumor antigen immunization. It has been previously reported that secretion of an appropriate amount of immunostimulatory cytokines in glioma tissues can recruit sufficient cytotoxic T cells for eliminating established brain tumors in animals immunized by s.c. administration of irradiated whole tumor cell vaccine (Iwadate, Y. et al., Cancer Res., 61: 8769-8774, 2001). Even in an immunologically privileged state, brain tumors can become susceptible to systemic immunization if the local expression of chemotactic molecules such as IL-2 effectively enhances the migration of effector cells to tumor tissues. In the present invention, the minus-strand RNA viral vector induced a substantive expression of IL-2 protein in glioma tissues, and the local concentration of the IL-2 protein reached a level required for significantly inducing immunocompetent cells and thereby suppressing the growth of brain tumors. Thus, the method of the present invention is an effective therapeutic means especially for immunologically privileged intracerebral tumors.

BRIEF DESCRIPTION OF THE DRAWINGS

FIG. 2 is a set of photographs showing X-gal staining patterns of rat brain tissue (upper panel) and 9L brain tumor that had grown for 7 days in the brain (lower panel), into which lacZ-SeV/ΔMΔF was administered in situ. X-gal staining was carried out 4, 7, and 14 days after vector administration (magnification: ×200). In both the brain tissue and the brain tumor, the maximal expression or accumulation of β-galactosidase was observed 7 days after vector injection, and the expression level was maintained on day 14.

FIG. 6 shows an immunohistochemical analysis of the IL-2 expression in 9L brain tumors. 9L brain tumors were intracerebrally administered with hIL2-SeV/ΔMΔF. Magnification: A, ×100; B, ×200. IL-2 protein is expressed diffusely.

BEST MODE FOR CARRYING OUT THE INVENTION

Figure 1:
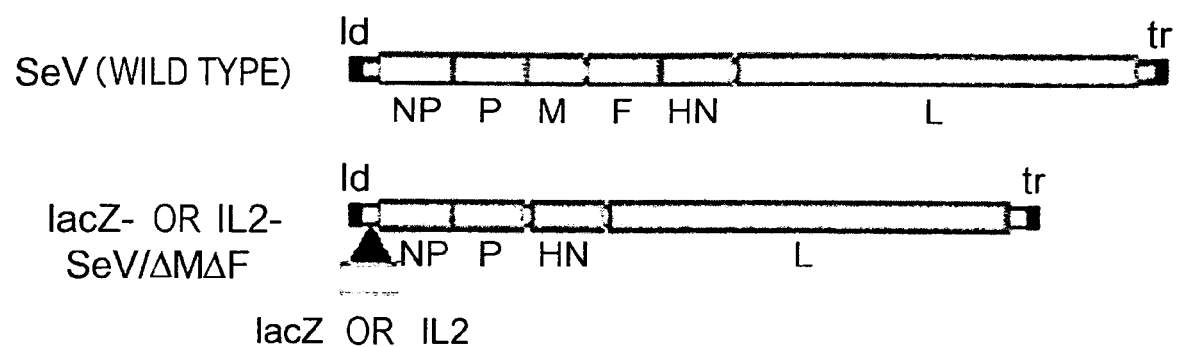
FIG. 1 is a schematic diagram showing the genomic structure of a Sendai virus vector. Wild-type SeV carrying lacZ or the human IL-2 gene, and an SeV vector lacking both the M and F genes are shown. Together with the end and start signals, which are SeV-specific transcriptional regulation signal sequences, the open reading frame of lacZ or the human IL-2 gene is inserted between the leader (ld) and the NP gene.

The present invention relates to methods of anti-tumor treatment comprising the step of introducing into tumor sites minus-strand RNA viral vectors that encode immunostimulatory cytokines or cells introduced with such vectors. Minus-strand RNA viral vectors that carry immunostimulatory cytokine genes induce immune response against a target (tumor) that has been introduced with the vectors and thus can significantly suppress tumor growth. Herein, the anti-tumor treatment means suppression of tumor development and/or growth. Specifically, the local administration of immunostimulatory cytokine-encoding minus-strand RNA viral vectors or cells introduced with the vectors to tumor sites, such as tumor tissues, potential sites for tumorigenesis, and tumor excision sites, can induce an anti-tumor immune response at the administration site and thereby suppress tumor development (including recurrence) or growth (including metastasis). The vector introduction can be achieved in vivo or ex vivo. For in-vivo introduction, the vector is injected directly into tumor sites. For ex-vivo introduction, the vector is introduced into cells outside the body and the cells are injected into tumor sites. A tumor site refers to a tumor itself, a tumor excision site, or a region adjacent thereto. Herein, the adjacent region refers to a region from which immunostimulatory cytokines secreted from cells introduced with the vector can reach the tumor or tumor excision site. The region is preferably within 5 mm, for example, within 3 mm, 2 mm, or 1 mm of a tumor or tumor excision site. The vector introduction may be conducted by dissolving or suspending a vector or cells introduced with the vector in a desired carrier (desired physiological aqueous solution, for example, culture medium, physiological saline, blood, plasma, serum, or body fluid), and then directly injecting them into a tumor or a region adjacent thereto. The method of the present invention allows effective treatment and prevention of tumors.

An important advantage of the minus-strand RNA viral vector-mediated gene delivery is that high efficiency gene delivery is achieved by a simple technique. In general, gene delivery mediated by a retroviral vector or the like has low efficiency, and therefore requires the vector be concentrated by centrifugation for optimal gene delivery. However, centrifugation often reduces the viral titer. Furthermore, a toxic agent, polybrene, is sometimes needed for high efficiency infection (Bunnell, B. A. et al., Proc. Natl. Acad. Sci. U S A, 1995, 92: 7739-7743; Chuck, A. S., Hum. Gene Ther., 1996, 7: 743-750; Chinnasamy, D. et al., Blood 2000, 96: 1309-1316; Fehse, B. et al., Br. J. Haematol., 1998, 102: 566-574). Furthermore, ex-vivo administration sometimes requires the step of selecting cells retaining the introduced gene after cell infection. In contrast, a minus-strand RNA viral vector can achieve a more superior gene delivery by merely contacting cells with the virus without a special agent. In addition, the infection efficiency is very high, and it is usually unnecessary to select cells that have been introduced with the gene with agents or such after vector infection. Furthermore, in the minus-strand RNA viral vector-mediated gene delivery, the optimal efficiency can be achieved in very short cell exposure time (30 minutes or shorter). In view of clinical situations, these characteristics enable to simplify the procedure for administration ex vivo, in vivo, and such, and to minimize procedure-dependent adverse effects such as cell damage.

When carrying out vector infection ex vivo, the MOI (multiplicity of infection; the number of infecting viruses per cell) is preferably in the range of 1 to 500, more preferably 2 to 300, even more preferably 3 to 200, still more preferably 5 to 100, yet more preferably 7 to 70. Contact between the vector and target cells needs only a short period of time, which may be, for example, 1 minute or longer, preferably 3 minutes or longer, 5 minutes or longer, 10 minutes or longer, or 20 minutes or longer, about 1 to about 60 minutes, and more specifically about 5 to 30 minutes. Alsoy, the contact time may be longer, for example, several days or longer. Cells derived from a patient to be administered may be used, for example, primary cultured fibroblast cells derived from a patient can be preferably used. Alternatively, xenogeneic cells and allogeneic cells can be used (Iwadate, Y. et al., Cancer Res., 61: 8769-8774, 2001). Xenogeneic or allogeneic cells are expected to be eliminated through host immune response after ex-vivo injection. The cells may be treated by UV, X-ray or gamma-ray irradiation, or such to make their dividing ability defective, and introduced ex vivo into tumors subsequently.

Immunostimulatory cytokines to be carried on the vector may be cytokines that induce differentiation and/or growth of immune cells and have anti-tumor activity. Such cytokines include cytokines that are produced by T cells, NK cells, monocytes, macrophages, or such, and induce differentiation and/or growth of T cells. An immunostimulatory cytokine gene can be isolated, for example, from a T-cell derived cDNA or such by PCR using primers designed based on the sequence of the gene. Cytokines having anti-tumor activity are well known to those skilled in the art. Such cytokine genes can be preferably used in the present invention. Specifically, immunostimulatory cytokines that are particularly preferably used in the present invention include interleukin-2 (IL-2), interleukin-4 (IL-4), interleukin-12 (IL-12), granulocyte-macrophage colony-stimulating factor (GM-CSF), and interleukin-23 (IL-23), which have been shown to elicit migration and adhesion of immune cells. Fas ligand (Fas-L) can also be used. IL-2 cDNA is described, for example, in Accession number NM_000586 (protein ID: NP_000577); IL-4 cDNA, for example, in Accession numbers M13982 (protein ID: AAA59149) and M23442 (protein ID: AAA59150); IL-12 (p 35+p 40), for example, in AF180562 (protein ID: AAD56385) (p 35) and AF180563 (protein ID: AAD56386) (p 40); GM-CSF, for example, in M11220 (protein ID: AAA52578) and A14305 (protein ID: CAA01150); IL-23(p 19+p 40), for example, in AF301620 (protein ID: AAG37232) (p 19) and AF180563 (p 40: identical to IL-12 p 40); and Fas-L, for example, in D38122 (protein ID: BAA07320). Therefore, a desired nucleic acid that encodes any of the amino acid sequences of the immunostimulatory cytokines described above can be incorporated into the vector, and used in the present invention.

The above cytokines have been reported to elicit migration and adhesion of immune cells. In particular, the effectiveness of IL-2, IL-4, and GM-CSF has been demonstrated in brain tumor animal models (IL-2: Iwadate, Y et al., Cancer Res., 61: 8769-8774 (2001); IL-2, IL-4, GM-CSF: Sampson, J. H. et al., Proc. Natl. Acad. Sci. USA 93, 10399-10404 (1996); GM-CSF: Herrlinger, U. et al., Cancer Gene Ther. 4, 345-352 (1997); IL-4: Seleh, M. et al., J. Natl. Cancer Inst. 91, 438-445, (1999); IL-4: Giezeman-Smits, K. M. et al., Cancer Res. 60, 2449-2457 (2000)). IL-23 has been demonstrated to be closely associated with the migration of immune cells in brain autoimmune diseases (Becher B. et al., J Clin Invest. 112(8), 1186-91 (2000)). Meanwhile, Fas-L has been shown to be effective as a chemoattractant (Silvestris F et al., Br J Haematol. 122(1) 39-52. (2003)). For activation of the immune system against tumors by IL-2 or such, see the following documents: Iwadate, Y. et al. (2000) Cancer Gene Ther. 7, 1263-1269; Iwadate, Y. et al. (2001) Cancer Res. 61, 8769-8774; Iwadate, Y. et al. (2002) Int. J. Mol. Med. 10, 741-747; Iwadate, Y. et al. (1997) Oncology (Basel) 54, 329-334; Iwadate, Y. et al. (2003) Int. J. Oncol. 23, 483-488.

Cytokine genes that are used in the present invention may be derived from human or other mammals, for example, mouse, rat, rabbit, pig, and primates, such as monkey. In the present invention, cytokines include variants of naturally occurring cytokines so long as they retain biological activity. Such variants include, for example, polypeptides with a deletion or addition of one to several amino acid residues (for example, 2, 3, 4, 5, or 6 residues) at the N- or C-terminus, and polypeptides with a substitution of one to several amino acid residues (for example, 2, 3, 4, 5, or 6 residues). The biological activity of a cytokine can be determined by known methods for assaying cytokine activity. Alternatively, the activity can be determined by the method for assaying tumor suppression described herein. Genes encoding variants with a biological activity equivalent to that of a naturally occurring cytokine are expected to exhibit an anti-tumor growth effect equivalent to that of the naturally occurring cytokine. Variants of a naturally occurring cytokine include fragments, analogues, and derivatives of a naturally occurring cytokine, and fusion proteins with other polypeptides (for example, a cytokine having a heterologous signal peptide and a polypeptide fused with an antibody fragment). Specifically, cytokines that are used in the present invention include polypeptides that comprise a sequence with a substitution, deletion, and/or addition of one or more amino acids in the amino acid sequence of a naturally occurring cytokine or fragment thereof, and have a biological activity equivalent to that of the naturally occurring cytokine. The fragment refers to a polypeptide comprising a portion of a naturally occurring cytokine polypeptide, which includes, for example, N- or C-terminal truncated forms. Cytokine fragments with the biological activity typically comprise a continuous region of 70% or more, preferably 80% or more, more preferably 90% or more of a naturally occurring polypeptide (in its mature form after secretion).

Amino acid sequence variants can be prepared, for example, by introducing mutations into DNAs that encode naturally occurring polypeptides (Walker and Gaastra, eds. (1983) Techniques in Molecular Biology (MacMillan Publishing Company, New York); Kunkel (1985) Proc. Natl. Acad. Sci. USA 82:488-492; Kunkel et al. (1987) Methods Enzymol. 154:367-382; Sambrook et al. (1989) Molecular Cloning: A Laboratory Manual (Cold Spring Harbor Laboratory Press, Plainview, N.Y.); U.S. Pat. No. 4,873,192). Guidance for substituting amino acids without affecting the polypeptide's biological activity includes, for example, Dayhoff et al. (1978) in Atlas of Protein Sequence and Structure (Natl. Biomed. Res. Found., Washington, D.C.)).

The number of amino acids altered is not specifically limited, but is, for example, 30% or less of the total amino acids in the mature form of a naturally occurring polypeptide, preferably 25% or less, more preferably 20% or less, even more preferably 15% or less, still more preferably 10% or less. It is, for example, 15 amino acids or less, preferably 10 amino acids or less, even more preferably 8 amino acids or less, still more preferably 5 amino acids or less, yet more preferably 3 amino acids or less. In amino acid substitution, substituting amino acids with those that have side chains with similar properties is expected to maintain a protein's original activity. This substitution is referred to as "conservative substitution" in the present invention. Conservative substitutions include substitutions between amino acids within the same group, such as basic amino acids (for example, lysine, arginine, and histidine), acidic amino acids (for example, aspartic acid, and glutamic acid), non-charged polar amino acids (for example, glycine, asparagine, glutamine, serine, threonine, tyrosine, and cysteine), nonpolar amino acids (for example, alanine, valine, leucine, isoleucine, proline, phenylalanine, methionine, and tryptophan), β-branched amino acids (for example, threonine, valine, and isoleucine), and aromatic amino acids (for example, tyrosine, phenylalanine, tryptophan, and histidine). Conservative substitutions also include, for example, substitutions between amino acids that give a positive score in the BLOSUM62 substitution matrix (S. Henikoff and J. G. Henikoff, 1992, Proc. Acad. Natl. Sci. USA 89: 10915-10919).

Cytokine variants also include polypeptides comprising an amino acid sequence with high homology to the amino acid sequence of a naturally occurring polypeptide. High homology amino acid sequences include those with an identity of, for example, 70% or higher, more preferably 75% or higher, even more preferably 80% or higher, still more preferably 85% or higher, yet more preferably 90% or higher, even still more preferably 93% or higher, yet still more preferably 95% or higher, yet still even more preferably 96% or higher. The amino acid sequence identity can be determined, for example, using the BLASTP program (Altschul, S. F. et al., 1990, J. Mol. Biol. 215: 403-410). For example, search is carried out on the BLAST web page of NCBI (National Center for Biotechnology Information) using default parameters, with all the filters including Low complexity turned off (Altschul, S. F. et al. (1993) Nature Genet. 3:266-272; Madden, T. L. et al. (1996) Meth. Enzymol. 266:131-141; Altschul, S. F. et al. (1997) Nucleic Acids Res. 25:3389-3402; Zhang, J. & Madden, T. L. (1997) Genome Res. 7:649-656). Sequence identity can be determined, for example, by comparing two sequences using the blast2sequences program to prepare an alignment of the two sequences (Tatiana A et al. (1999) FEMS Microbiol Lett. 174:247-250). Gaps are treated in the same way as mismatches. For example, an identity score is calculated in view of the entire amino acid sequence of a naturally occurring cytokine (its mature form after secretion). Specifically, the ratio of the number of identical amino acids to the total number of amino acids in a naturally occurring cytokine (mature form) is calculated.

Preferred variants include polypeptides encoded by nucleic acids that hybridize under stringent conditions with the entire or a portion of the coding region of a naturally occurring cytokine gene, and have a biological activity equivalent to that of the naturally occurring cytokine. When hybridization is used, such a variant can be identified, for example, by preparing a probe either from a nucleic acid that comprises the sequence of the coding region of a naturally occurring cytokine gene or the complementary sequence thereof, or from a nucleic acid to be hybridized, and then detecting whether the probe hybridizes to the other nucleic acid. Stringent hybridization conditions are, for example, hybridization at 60° C., preferably at 65° C., more preferably at 68° C. in a solution containing 5×SSC, 7% (W/V) SDS, 100 μg/ml denatured salmon sperm DNA, and 5× Denhardt's solution (1× Denhardt's solution contains 0.2% polyvinylpyrrolidone, 0.2% bovine serum albumin, and 0.2% Ficoll); and washing twice at the same temperature as the hybridization while shaking in 2×SSC, preferably 1×SSC, more preferably 0.5×SSC, still more preferably 0.1×SSC.

The most preferable cytokine used in the present invention is interleukin (IL)-2. IL-2 is a cytokine that functions as a ligand for IL-2 receptors (IL-2 receptors α, β, and γ) and regulates the growth and differentiation of T cells (Kuziel, W. A. and Gree, W. C. (1991), Interleukin-2, in The Cytokine Handbook, A. Thompson (Ed.), San Diego, Calif., Academic Press, pages 83-102; Waldmann, T. A., 1993, Immunol. Today, 14:264). IL-2 is produced mainly by CD4⁺ T cells, and functions as an autocrine growth factor. IL-2 also acts on other T lymphocytes including both CD4⁺ and CD8⁺ cells. IL-2 also induces local inflammatory responses which lead to the activation of both subsets of helper and cytotoxic T cells. In addition, IL-2 stimulates the growth and activity of natural killer (NK) cells. Tumor cells that are altered to express IL-2 stimulate immune response against tumors and thereby suppress tumor growth. The nucleotide sequence of human IL-2 (mature form) cDNA is exemplified in sequence SEQ ID NO: 1, and the amino acid sequence of IL-2 is exemplified in SEQ ID NO: 2. Genes encoding the amino acid sequence of SEQ ID NO: 2 can be preferably used in the present invention.

Meanwhile, many biological active IL-2 variants are known to those skilled in the art. IL-2 variants that can be used in the present invention include, for example, those described in European Patent Application Nos. 136,489, 91,539, 88,195, and 109,748; U.S. Pat. Nos. 4,518,584, 4,588,584, 4,752,585, 4,931,543, and 5,206,344; International Patent Application WO 99/60128; Japanese Patent Application Kokai Publication (JP-A) No. S61-78799 (unexamined, published Japanese patent application); and Wang, et al. Science (1984) 224:1431-1433. Such variants include, for example, an IL-2 fragment lacking the N-terminal Ala, an IL-2 fragment lacking four amino acids (JP-A No. S60-126088), a carboxyl terminal-truncated IL-2 fragment (JP-A No. S60-126088), a polypeptide in which a neutral amino acid, such as serine or alanine, has been substituted for cysteine 125 in the natural occurring polypeptide after secretion (des-ala-1, ser-125 IL-2, or des-ala-1, ala-125 IL-2) (U.S. Patent Nos. 4,518, 584 and 4,588,584), and a polypeptide in which a neutral amino acid, such as alanine, has been substituted for methionine 104 (des-ala-1, ala-104). In addition to those described above, desired variants retaining the biological activity of IL-2 may also be used. The IL-2 biological activity of a variant can be confirmed, for example, by testing its ability to stimulate the growth of IL-2-dependent cytotoxic or helper T cells using known methods (Gillis et al., J. immunol. (1978) 120:2027-2032; Watson, J., J. exp. Med. (1979) 1570:1510-1519).

cDNAs that encode the above-described cytokines are used to construct recombinant minus-strand RNA viruses expressing the cytokines. Herein, a minus-strand RNA virus refers to viruses that include a minus strand (an antisense strand corresponding to a sense strand encoding viral proteins) RNA as the genome. The minus-strand RNA is also referred to as negative strand RNA. The minus-strand RNA virus used in the present invention particularly includes single-stranded minus-strand RNA viruses (also referred to as non-segmented minus-strand RNA viruses). The "single-strand negative strand RNA virus" refers to viruses having a single-stranded negative strand [i. e., a minus strand] RNA as the genome. Such viruses include viruses belonging to Paramyxoviridae (including the genera *Paramyxovirus, Morbillivirus, Rubulavirus*, and *Pneumovirus*), Rhabdoviridae (including the genera *Vesiculovirus, Lyssavirus*, and *Ephemerovirus*), Filoviridae, Orthomyxoviridae, (including Influenza viruses A, B, and C, and Thogoto-like viruses), Bunyaviridae (including the genera *Bunyavirus, Hantavirus, Nairovirus*, and *Phlebovirus*), Arenaviridae, and the like.

In addition, the minus-strand RNA viral vector refers to a minus-strand RNA virus-based vehicle for introducing genes into cells. Herein, "infectivity" refers to the capability of a minus-strand RNA viral vector to maintain cell-adhesion ability and introduce a gene carried by the vector to the inside of the cell to which the vector has adhered. The minus-strand RNA viral vector of this invention may be transmissible or may be a nontransmissible defective-type vector. "Transmissible" means that when a viral vector infects a host cell, the virus is replicated in the cell to produce infectious virions.

"Recombinant virus" refers to a virus produced through a recombinant polynucleotide, or an amplification product thereof. "Recombinant polynucleotide" refers to a polynucleotide in which nucleotides are not linked at one or both ends as in the natural condition. Specifically, a recombinant polynucleotide is a polynucleotide in which the linkage of the polynucleotide chain has been artificially modified (cleaved and/or linked). Recombinant polynucleotides can be produced by using gene recombination methods known in the art in combination with polynucleotide synthesis, nuclease treatment, ligase treatment, etc. A recombinant virus can be produced by expressing a polynucleotide encoding a viral genome constructed through gene manipulation and reconstructing the virus. For example, methods for reconstructing a virus from cDNA that encodes the viral genome are known (Y. Nagai, A. Kato, Microbiol. Immunol., 43, 613-624 (1999)).

In the present invention, "gene" refers to a genetic substance, a nucleic acid encoding a transcriptional unit. Genes may be RNAs or DNAs. In this invention, a nucleic acid encoding a protein is referred to as a gene of that protein. Further, in general, a gene may not encode a protein. For example, a gene may encode a functional RNA, such as a ribozyme or antisense RNA. Generally, a gene may be a naturally-occurring or artificially designed sequence. Furthermore, in the present invention, "DNA" includes both single-stranded and double-stranded DNAs. Moreover, "encoding a protein" means that a polynucleotide includes an ORF that encodes an amino acid sequence of the protein in a sense or antisense strand, so that the protein can be expressed under appropriate conditions.

A minus-strand RNA virus particularly preferably used in the context of the present invention includes, for example, Sendai virus, Newcastle disease virus, mumps virus, measles virus, respiratory syncytial virus (RS virus), rinderpest virus, distemper virus, simian parainfluenza virus (SV5), and human parainfluenza viruses 1, 2, and 3 belonging to *Paramyxoviridae*; influenza virus belonging to *Orthomyxoviridae*; and vesicular stomatitis virus and rabies virus belonging to *Rhabdoviridae*.

Further examples of virus that may be used in the context of the present invention include those selected from the group consisting of: Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), Nipah virus (Nipah), human parainfluenza virus-2 (HPIV-2), simian parainfluenza virus 5 (SV5), human parainfluenza virus-4a (HPIV-4a), human parainfluenza virus-4b (HPIV-4b), mumps virus (Mumps), and Newcastle disease virus (NDV). A more preferred example is a virus selected from the group consisting of Sendai virus (SeV), human parainfluenza virus-1 (HPIV-1), human parainfluenza virus-3 (HPIV-3), phocine distemper virus (PDV), canine distemper virus (CDV), dolphin molbillivirus (DMV), peste-des-petits-ruminants virus (PDPR), measles virus (MV), rinderpest virus (RPV), Hendra virus (Hendra), and Nipah virus (Nipah).

More preferably, viruses of the present invention are preferably those belonging to Paramyxoviridae (including *Respirovirus, Rubulavirus*, and *Morbillivirus*) or derivatives thereof, and more preferably those belonging to the genus *Respirovirus* (also referred to as *Paramyxovirus*) or derivatives thereof. The derivatives include viruses that are genetically-modified or chemically-modified in a manner not to impair their gene-transferring ability. Examples of viruses of the genus *Respirovirus* applicable to this invention are human parainfluenza virus-1 (HPIV-1), human parainfluenza virus-3 (HPIV-3), bovine parainfluenza virus-3 (BPIV-3), Sendai virus (also referred to as murine parainfluenza virus-1), and simian parainfluenza virus-10 (SPIV-10). A more preferred paramyxovirus in this invention is the Sendai virus. These viruses may be derived from natural strains, wild strains, mutant strains, laboratory-passaged strains, artificially constructed strains, or the like.

Genes harbored on a minus-strand RNA viral vector are situated in the antisense direction in the viral genomic RNA. Viral genomic RNA refers to RNA that has the finction to form a ribonucleoprotein (RNP) with the viral proteins of a minus-strand RNA virus. Genes contained in the genome are expressed by the RNP, genomic RNA is replicated, and daughter RNPs are formed. In general, in the minus-strand RNA viral genome, viral genes are arranged as antisense sequences between the 3'—leader region and the 5'—trailer region. Between the ORFs of respective genes are a transcription ending sequence (E sequence)—intervening sequence (I sequence)—transcription starting sequence (S sequence), such that RNA encoding the ORF of each gene is transcribed as an individual cistron. Genomic RNAs in a virus of this invention comprise the antisense RNA sequences encoding N (nucleocapsid)—, P (phospho)—, and L (large)—proteins, which are viral proteins essential for the expression of the group of genes encoded by an RNA, and for the autonomous replication of the RNA itself. The genomic RNAs may or may not encode M (matrix) proteins, which is essential for virion formation. Further, the RNAs may or may not encode envelope proteins essential for virion infection. Minus-strand RNA viral envelope proteins include F (fusion) protein that causes cell membrane fusion, and HN (hemagglutinin-neuraminidase) protein which is essential for viral adhesion to cells. However, HN protein is not required for the infection of certain types of cells (Markwell, M. A. et al., Proc. Natl. Acad. Sci. USA 82(4): 978-982 (1985)), and infection is achieved with F protein only. The RNAs may encode envelope proteins other than F protein and/or HN protein. Thus, the genomic RNAs may be naturally-occurring viral genomes that are appropriately modified (WO 00/70055 and WO 00/70070).

Minus-strand RNA viruses of this invention may be, for example, complexes of minus-strand RNA viral genomic RNAs and viral proteins, that is, ribonucleoproteins (RNPs). RNPs can be introduced into cells, for example, in combination with desired transfection reagents. Specifically, such RNPs are complexes comprising a minus-strand RNA viral genomic RNA, N protein, P protein, and L protein. On introducing an RNP into cells, cistrons encoding the viral proteins are transcribed from the genomic RNA by the action of viral proteins, and, at the same time, the genome itself is replicated to form daughter RNPs. Replication of a genomic RNA can be confirmed by using RT-PCR, Northern blot hybridization, or the like to detect an increase in the copy number of the RNA.

Further, minus-strand RNA viruses of this invention are preferably infectious minus-strand RNA viral virions. "Virion" means a microparticle comprising a nucleic acid released from a cell by the action of viral proteins. Infectivity refers to the ability of a minus-strand RNA virus, which retain cell adhesion and membrane-fusion abilities, to introduce nucleic acids inside the virus into cells to which the virion has adhered. The virion of a minus-strand RNA virus has a structure, in which the above-described RNP comprising genomic RNA and viral proteins is enclosed in a lipid membrane (referred to as an envelope) derived from cell membrane. Minus-strand RNA viruses of this invention may be transmissible or may be a nontransmissible defective-type virus. "Transmissible" means that when a virus is introduced into a host cell, the virus can replicate itself within the cell to produce infectious virions.

Genes of Paramyxovirinae viruses are commonly listed as follows. In general, NP gene is also listed as "N gene."

| Respirovirus | NP | P/C/V | M | F | HN | — | L |
|---|---|---|---|---|---|---|---|
| Rubulavirus | NP | P/V | M | F | HN | (SH) | L |
| Morbillivirus | NP | P/C/V | M | F | H | — | L |

For example, the database accession numbers for the nucleotide sequences of each of the Sendai virus genes are: M29343, M30202, M30203, M30204, M51331, M55565, M69046, and X17218 for NP gene; M30202, M30203, M30204, M55565, M69046, X00583, X17007, and X17008 for P gene; D11446, K02742, M30202, M30203, M30204, M69046, U31956, X00584, and X53056 for M gene; D00152, D11446, D17334, D17335, M30202, M30203, M30204, M69046, X00152, and X02131 for F gene; D26475, M12397, M30202, M30203, M30204, M69046, X00586, X02808, and X56131 for HN gene; and D00053, M30202, M30203, M30204, M69040, X00587, and X58886 for L gene. Examples of viral genes encoded by other viruses are: CDV, AF014953; DMV, X75961; HPIV-1, D01070; HPIV-2, M55320; HPIV-3, D10025; Mapuera, X85128; Mumps, D86172; MV, K01711; NDV, AF064091; PDPR, X74443; PDV, X75717; RPV, X68311; SeV, X00087; SV5, M81442; and Tupaia, AF079780 forN gene; CDV, X51869; DMV, Z47758; HPIV-1, M74081; HPIV-3, X04721; HPIV-4a, M55975; HPIV-4b, M55976; Mumps, D86173; MV, M89920; NDV, M20302; PDV, X75960; RPV, X68311; SeV, M30202; SV5, AF052755; and Tupaia, AF079780 for P gene; CDV, AF014953; DMV, Z47758; HPIV-1, M74081; HPIV-3, D00047; MV, ABO16162; RPV, X68311; SeV,AB005796; and Tupaia, AF079780 for C gene; CDV, M12669; DMV, Z30087; HPIV-1, S38067; HPIV-2, M62734; HPIV-3, D00130; HPIV-4a, D10241; HPIV-4b, D10242; Mumps, D86171; MV, AB012948; NDV, AF089819; PDPR, Z47977; PDV, X75717; RPV, M34018; SeV, U31956; and SV5, M32248 for M gene; CDV, M21849; DMV, AJ224704; HPN-1, M22347; HPIV-2, M60182; HPIV-3, X05303; HPIV-4a, D49821; HPIV-4b, D49822; Mumps, D86169; MV, AB003178; NDV, AF048763; PDPR, Z37017; PDV, AJ224706; RPV, M21514; SeV, D17334; and SV5, AB021962 for F gene; and, CDV, AF112189; DMV, AJ224705; HPIV-1, U709498; HPIV-2, D000865; HPIV-3, AB012132; HPIV-4A, M34033; HPIV-4B, AB006954; Mumps, X99040; MV, K01711; NDV, AF204872; PDPR, Z81358; PDV, Z36979; RPV, AF132934; SeV, U06433; and SV-5, S76876 for HN (H or G) gene. However, multiple strains are known for each virus, and there exist genes that comprise sequences other than those cited above as a result of strain variation.

ORFs encoding these viral proteins and ORFs of foreign genes are arranged in the antisense direction in the genomic RNA via the above-described E-I-S sequence. The ORF closest to the 3'—end of the genomic RNA requires only an S sequence between the 3'—leader region and the ORF, and does not require an E or I sequence. Further, the ORF closest to the 5'—end of the genomic RNA requires only an E sequence between the 5'—trailer region and the ORF, and does not require an I or S sequence. Furthermore, two ORFs can be transcribed as a single cistron, for example, by using an internal ribosome entry site (IRES) sequence. In such a case, an E-I-S sequence is not required between these two ORFs. For example, in wild type paramyxoviruses, a typical RNA genome includes a 3'—leader region, six ORFs encoding the N, P, M, F, HN, and L proteins in the antisense direction in this order, and a 5'—trailer region on the other end. The orientation of the viral gene in the genomic RNAs of the present invention is not restricted, but similarly to the wild type viruses, it is preferable that ORFs encoding the N, P, M, F, HN, and L proteins are arranged after the 3'—leader region and before the 5'—trailer region. Certain types of viruses have different viral genes, but even in such cases, it is preferable that each gene be arranged as in the wild type, as described above. In general, vectors maintaining the N, P, and L genes can autonomously express genes from the RNA genome in cells and the genomic RNA is replicated. Furthermore, by the action of genes such as the F and HN genes which encode envelope proteins and the M gene, infectious virions are formed and released to the outside of the cells. Thus, such vectors become transmissible viral vectors. A cytokine gene to be carried by the vectors may be inserted into a non-protein-coding region in this genome, as described below.

Further, a minus-strand RNA virus of this invention may be deficient in any of the wild type virus genes. For example, a viral vector in which the M, F, or HN gene, or any combination thereof is inactivated or deleted, can be preferably used in this invention. Such viruses can be reconstituted, for example, by externally supplying the products of the deficient genes. Similar to wild type viruses, the viruses thus prepared adhere to host cells and cause cell fusion, but they cannot form daughter virions that retain the same infectivity as the original vector, because the viral genome introduced into cells is deficient in viral genes. Therefore, such vectors are useful as safe viral vectors that can only introduce genes once. Examples of genes in which the genome may be deficient are the F gene, HN gene, M gene, or any combination thereof. For example, recombinant viruses can be reconstituted by trans-fecting host cells with a plasmid expressing a recombinant minus-strand RNA viral genome deficient in the F gene, along with an F protein expression vector and expression vectors for the NP, P, and L proteins (WO00/70055, WO00/70070, and WO03/025570; Li, H.-O. et al., J. Virol. 74(14) 6564-6569 (2000)). Viruses can also be produced, for example, using host cells that have incorporated the F gene into their chromosomes. These proteins, which are expressed in virus-producing cells, do not need to have the same amino acid sequences as the viral sequences, and a mutant or homologous gene from another virus may be used as a substitute, so long as the activity in nucleic acid introduction is the same as, or greater than, that of the natural type.

Further, recombinant viruses that include an envelope protein other than that of the virus from which the viral genome was derived, may be prepared as viral vectors used in this invention. For example, when reconstituting a virus, a recombinant virus including a desired envelope protein can be generated by expressing an envelope protein other than the envelope protein originally encoded by the basic viral genome. Such proteins are not particularly limited. A desired protein that confers an ability to infect cells may be used. Examples of such proteins include the envelope proteins of other viruses, for example, the G protein of vesicular stomatitis virus (VSV-G). The VSV-G protein may be derived from an arbitrary VSV strain. For example, VSV-G proteins derived from Indiana serotype strains (J. Virology 39: 519-528 (1981)) may be used, but the present invention is not limited thereto. Furthermore, the present vector may include any arbitrary combination of envelope proteins derived from other viruses. Preferred examples of such proteins are envelope proteins derived from viruses that infect human cells. Such proteins are not particularly limited, and include retroviral amphotropic envelope proteins and the like. For example, the envelope proteins derived from mouse leukemia virus (MuLV) 4070A strain can be used as the retroviral amphotropic envelope proteins. In addition, envelope proteins derived from MuMLV 10A1 strain may also be used (for example, pCL-10A1 (Imgenex) (Naviaux, R. K. et al., J. Virol. 70:5701-5705 (1996)). The proteins of *Herpesviridae* include, for example, gB, gD, gH, and gp85 proteins of herpes simplex viruses, and gp350 and gp220 proteins of EB virus. The proteins of *Hepadnaviridae* include the S protein of hepatitis B virus. These proteins may be used as fusion proteins in which the extracellular domain is linked to the intracellular domain of the F or HN protein. As described above, the viral vectors used in this invention include pseudotype viral vectors that include envelope proteins, such as VSV-G derived from viruses other than the virus from which the genome was derived. If the viral vectors are designed such that these envelope proteins are not encoded in RNA genomes, the proteins will never be expressed after virion infection of the cells.

Furthermore, the viral vectors used in this invention may be, for example, vectors that include on the envelope surface thereof, proteins such as adhesion factors capable of adhering to specific cells, ligands, receptors, antibodies or fragments, or vectors that include a chimeric protein with these proteins in the extracellular domain and polypeptides derived from the virus envelope in the intracellular domain. Thus, the specificity of the viral vector infection can be controlled. These proteins may be encoded in the viral genome, or supplied through the expression of genes not in the viral genome (for example, genes carried by other expression vectors, or genes in the host chromosomes) at the time of virus reconstitution.

Further, in the viral vectors, any viral gene contained in the virus may be modified from the wild type gene in order to reduce the immunogenicity caused by viral proteins, or to enhance RNA transcriptional or replicational efficiency, for example. Specifically, for example, modifying at least one of the replication factors N, P, and L genes, is considered to enhance transcriptional or replicational function. Furthermore, although the HN protein, which is an envelope protein, has both hemagglutinin activity and neuraminidase activity, it is possible, for example, to improve viral stability in blood if the former activity is attenuated, and infectivity can be controlled if the latter activity is modified. Further, it is also possible to control membrane fusion ability by modifying the F protein. For example, the epitopes of the F protein and/or HN protein, which can be cell surface antigenic molecules, can be analyzed, and using this, recombinant viral vectors with reduced antigenicity to these proteins can be prepared.

Furthermore, the minus-strand RNA viral vector may be deficient in one or more accessory genes. For example, by knocking out the V gene, one of the SeV accessory genes, the pathogenicity of SeV toward hosts such as mice is remarkably reduced, without hindering gene expression and replication in cultured cells (Kato, A. et al., 1997, J. Virol. 71: 7266-7272; Kato, A. et al., 1997, EMBO J.16: 578-587; Curran, J. et al., WO01/04272, EP1067179). Such attenuated vectors are particularly useful as low-toxic viral vectors for in vivo or ex vivo gene transfer.

Minus-strand RNA viruses are excellent gene transfer vectors. They do not have DNA phase and carry out transcription and replication only in the host cytoplasm, and consequently, chromosomal integration does not occur (Lamb, R. A. and Kolakofsky, D., Paramyxoviridae: The viruses and their replication. In: Fields B N, Knipe D M, Howley P M, (eds). Fields of Virology. Vol.2. Lippincott—Raven Publishers: Philadelphia, 1996, pp. 1177-1204). Therefore, safety issues such as transformation and immortalization due to chromosomal abberation do not occur. This characteristic of minus-strand RNA viruses contributes greatly to safety when it is used as a vector. For example, results on foreign gene expression show that even after multiple continuous passages of SeV, almost no nucleotide mutation is observed. This suggests that the viral genome is highly stable and the inserted foreign genes are stably expressed over long periods of time (Yu, D. et al., Genes Cells 2, 457-466 (1997)). Further, there are qualitative advantages associated with SeV not having a capsid structural protein, such as packaging flexibility and insert gene size, suggesting that minus-strand RNA viral vectors may become a novel class of highly efficient vectors for human anti-tumor gene therapy. Transmissible SeV vectors are capable of introducing foreign genes of up to at least 4 kb in size, and can simultaneously express two or more kinds of genes by adding the transcriptional units.

Further, SeV is known to be pathogenic in rodents causing pneumonia, but is not pathogenic for human. This is also supported by a previous report that nasal administration of wild type SeV does not have severely harmful effects on non-human primates (Hurwitz, J. L. et al., Vaccine 15: 533-540, 1997; Bitzer, M. et al., J. Gene Med. 5: 543-553, 2003). These SeV characteristics suggest that SeV vectors can be applied therapeutically on humans, supporting the proposition that SeV vectors are a promising choice of gene therapy for human cancers.

Viral vectors of this invention encode cytokine genes in their genomic RNA. A recombinant viral vector harboring a cytokine gene is obtained by inserting a cytokine gene into an above-described viral vector genome. The cytokine gene can be inserted at any desired position in a non-protein-coding region of the virus genome, for example. The above nucleic acid can be inserted, for example, between the 3'—leader region and the viral protein ORF closest to the 3'—end; between each of the viral protein ORFs; and/or between the viral protein ORF closest to the 5'—end and the 5'—trailer region in genomic DNA. Further, in genomes deficient in the F or HN gene or the like, nucleic acids encoding the cytokine genes can be inserted into those deficient regions. When introducing a foreign gene into a paramyxovirus, it is desirable to insert the gene such that the chain length of the polynucleotide to be inserted into the genome will be a multiple of six (Journal of Virology, Vol. 67, No. 8, 4822-4830, 1993). An E-I-S sequence should be arranged between the inserted cytokine gene and the viral ORF. Two or more foreign genes can be inserted in tandem via E-I-S sequences.

Expression levels of a foreign gene carried in a vector can be controlled using the type of transcriptional initiation sequence added upstream (to the 3'—side of the minus strand (negative strand)) of the gene (WO01/18223). The expression levels can also be controlled by the position at which the foreign gene is inserted in the genome: the nearer to the 3'—end of the minus strand the insertion position is, the higher the expression level; while the nearer to the 5'—end the insertion position is, the lower the expression level. Thus, to obtain a desired gene expression level, the insertion position of a foreign gene can be appropriately controlled such that the combination with genes encoding the viral proteins before and after the foreign gene is most suitable. In general, since a high foreign gene expression level is thought to be advantageous, it is preferable to link the foreign gene to a highly efficient transcriptional initiation sequence, and to insert it near the 3'—end of the minus strand genome. Specifically, a foreign gene is inserted between the 3'—leader region and the viral protein ORF closest to the 3'—end. Alternatively, a foreign gene may be inserted between the ORFs of the viral protein gene closest to the 3'—end and the second closest viral protein gene, or between the ORFs of the second and third closest viral protein genes. In wild type paramyxoviruses, the viral protein gene closest to the 3'—end of the genome is the N gene, the second closest gene is the P gene, and the third closest gene is M gene. Alternatively, when a high level of expression of the introduced gene is undesirable, the gene expression level from the viral vector can be suppressed to obtain an appropriate effect, for example, by inserting the foreign gene at a site as close as possible to the 5'—side of the minus strand genome, or by selecting an inefficient transcriptional initiation sequence.

For example, a desired S sequence of a minus-strand RNA virus may be used as the S sequence to be attached when inserting a foreign gene-encoding nucleic acid into the genome. The sequence 3'-UCCCWVUUWC-5' (W=A or C; V=A, C, or G) (SEQ ID NO: 3) can be preferably used for Sendai viruses. Particularly preferred sequences are 3'-UCCCAGUUUC-5' (SEQ ID NO: 4), 3'-UCCCACUUAC-5' (SEQ ID NO: 5), and 3'-UCCCACUUUC-5' (SEQ ID NO: 6). When shown as plus strand-encoding DNA sequences, these sequences are 5'-AGGGTCAAAG-3' (SEQ ID NO: 7), 5'-AGGGTGAATG-3' (SEQ ID NO: 8), and 5'-AGGGTGAAAG-3' (SEQ ID NO: 9). A preferred E sequence of a Sendai viral vector is, for example, 3'-AUUCUUUUUU-5' (SEQ ID NO: 10) or 5'-TAAGAAAAAA-3' (SEQ ID NO: 11) for the plus strand-encoding DNA. An I sequence may be, for example, any three nucleotides, specifically 3'-GAA-5' (5'-CTT-3' in the plus strand DNA).

To prepare a minus-strand RNA viral vector, a cDNA encoding a genomic RNA of a minus-strand RNA virus is transcribed in mammalian cells, in the presence of viral proteins (i.e., N, P, and L proteins) essential for reconstitution of an RNP including the genomic RNA of the minus-strand RNA virus. Viral RNP can be reconstituted by producing either the minus-strand genome (that is, the same antisense strand as the viral genome) or the plus strand (antigenome, the complementary strand of the genomic RNA). For increasing the efficiency of vector reconstitution, it is more preferable to produce the plus strand. The RNA terminals preferably reflect the terminals of the 3'—leader sequence and 5'—trailer sequence as accurately as possible, as in the natural viral genome. To accurately regulate the 5'—end of the transcript, for example, the RNA polymerase may be expressed within a cell using the recognition sequence of T7 RNA polymerase as a transcription initiation site. To regulate the 3'—end of the transcript, for example, a self-cleaving ribozyme can be encoded at the 3'—end of the transcript, allowing accurate cleavage of the 3'—end with this ribozyme (Hasan, M. K. et al., J. Gen. Virol. 78: 2813-2820, 1997; Kato, A. et al., 1997, EMBO J. 16: 578-587; and Yu, D. et al., 1997, Genes Cells 2: 457-466). An auto-cleaving ribozyme derived from the antigenomic strand of delta hepatitis virus can be used.

For example, a recombinant Sendai virus can be constructed as follows, according to descriptions in: Hasan, M.

K. et al., J. Gen. Virol. 78: 2813-2820, 1997; Kato, A. et al., 1997, EMBO J. 16: 578-587; Yu, D. et al., 1997, Genes Cells 2: 457-466; or the like.

First, a DNA sample comprising a cDNA sequence of a foreign gene of interest is prepared. The DNA sample is preferably one that can be confirmed to be a single plasmid by electrophoresis at a concentration of 25 ng/µl or more. The following explains a case using a Not I site to insert a foreign gene into a DNA encoding a viral genomic RNA, with reference to examples. When a Not I recognition site is included in a target cDNA nucleotide sequence, the base sequence is altered using site-directed mutagenesis or the like, such that the encoded amino acid sequence does not change, and the Not I site is preferably excised in advance. The gene fragment of interest is amplified from this sample by PCR, and then recovered. By adding the Not I site to the 5' regions of a pair of primers, both ends of the amplified fragments become Not I sites. E-I-S sequences are designed to be included in primers such that, after a foreign gene is inserted into the viral genome, one E-I-S sequence is placed between the foreign gene ORF and each side of the viral gene ORF. The length of the synthesized DNA is designed such that the chain length of the last fragment to be inserted, which contains the added E-I-S sequences, will become a multiple of six nucleotides (the so-called "rule of six"); Kolakofski, D., et al., J. Virol. 72:891-899, 1998; Calain, P. and Roux, L., J. Virol. 67:4822-4830, 1993; Calain, P. and Roux, L., J. Virol. 67: 4822-4830, 1993). For an E-I-S sequence, the Sendai virus S, I, and E sequences, for example, 5'-CTTTCACCCT-3' (SEQ ID NO: 12), 5'-AAG-3', and 5'-TTTTTCTTACTACGG-3' (SEQ ID NO: 13), respectively, are used in, for example, the 3'-side of the oligo DNA insertion fragment.

PCR can be performed according to conventional methods, using Taq polymerase or other DNA polymerases. The amplified fragments of interest may be digested with Not I, and then inserted into the Not I site of plasmid vectors such as pBluescript. The nucleotide sequences of PCR products thus obtained are confirmed with a sequencer, and plasmids that include the correct sequence are selected. The inserted fragment is excised from these plasmids using Not I, and cloned into the Not I site of a plasmid composed of genomic cDNA. A recombinant Sendai virus cDNA can also be obtained by inserting the fragment directly into the Not I site of a genomic cDNA, without using a plasmid vector.

For example, a recombinant Sendai virus genomic cDNA can be constructed according to methods described in the literature (Yu, D. et al., Genes Cells 2: 457-466, 1997; Hasan, M. K. et al., J. Gen. Virol. 78: 2813-2820, 1997). For example, a double-stranded DNA is synthesized to have an E-I-S sequence attached to the 3' end of the sense strand of the foreign gene. The DNA is inserted immediately 3' of a desired S sequence in a cDNA encoding the plus strand of the genome. For example, on a cDNA that encodes the plus strand genome, a restriction site (e.g., Not I site) is first placed between a sequence encoding the desired viral protein gene and an S sequence that transcribes the gene. A DNA encoding a foreign gene-E-I-S sequence can then be inserted into the restriction site (Tokusumi, T. et al. Virus Res 86(1-2), 33-8 (2002)).

A viral vector can be reconstituted by transcribing a DNA encoding a genomic RNA of a recombinant virus thus prepared, in cells in the presence of the above-described viral proteins (L, P, and N). The recombinant viruses can be reconstituted by methods known in the art (WO97/16539; WO97/16538; WO03/025570; Durbin, A. P. et al., 1997, Virology 235: 323-332; Whelan, S. P. et al., 1995, Proc. Natl. Acad. Sci. USA 92: 8388-8392; Schnell. M. J. et al., 1994, EMBO J. 13: 4195-4203; Radecke, F. et al., 1995, EMBO J. 14: 5773-5784; Lawson, N. D. et al., Proc. Natl. Acad. Sci. USA 92: 4477-4481; Garcin, D. et al., 1995, EMBO J. 14: 6087-6094; Kato, A. et al., 1996, Genes Cells 1: 569-579; Baron, M. D. and Barrett, T., 1997, J. Virol. 71: 1265-1271; Bridgen, A. and Elliott, R. M., 1996, Proc. Natl. Acad. Sci. USA 93: 15400-15404). With these methods, minus strand RNA viruses including parainfluenza virus, vesicular stomatitis virus, rabies virus, measles virus, rinderpest virus, and Sendai virus can be reconstituted from DNA. The viruses of this invention can be reconstituted according to these methods. When a viral genome-encoding DNA is made F gene, HN gene, and/or M gene deficient, such DNAs do not form infectious virions as is. However, infectious virions can be formed by separately introducing host cells with these deficient genes, and/or genes encoding the envelope proteins of other viruses, and then expressing these genes therein (Hirata, T. et al., 2002, J. Virol. Methods, 104: 125-133; Inoue, M. et al., 2003, J. Virol. 77: 6419-6429). The present invention is related to the use of minus-strand RNA viral vectors encoding an immunostimulatory cytokine for preparation of anti-tumor agents. The present invention is also related to the use of viral genomic RNAs of minus-strand RNA viruses that encode an immunostimulatory cytokine or the use of DNAs encoding complementary RNAs thereof, for preparation of anti-tumor agents. The anti-tumor agents of the present invention are used as pharmaceuticals for preventing and/or treating tumors.

Specifically, the viruses can be prepared by the steps of: (a) transcribing cDNAs encoding genomic RNAs of minus-strand RNA viruses (minus-strand RNAs), or complementary strands thereof (plus-strands), in cells expressing N, P, and L proteins; and (b) harvesting complexes containing the genomic RNAs from the cells or culture supernatants thereof. For transcription, a DNA encoding a genomic RNA is linked downstream of an appropriate promoter. The genomic RNA thus transcribed is replicated in the presence of N, L, and P proteins to form an RNP complex containing these proteins. Then, in the presence of M, HN, and F proteins, virions enclosed in an envelope are formed. For example, a DNA encoding a genornic RNA can be linked downstream of a T7 promoter, and transcribed to RNA by T7 RNA polymerase. Any desired promoter can be used as a promoter, in addition to those including a T7 polymerase recognition sequence. Alternatively, RNA transcribed in vitro may be transfected into cells.

Enzymes essential for the initial transcription of genomic RNA from DNA, such as T7 RNA polymerase, can be supplied by transducing the plasmid or viral vectors that express them, or, for example, by incorporating the gene into a chromosome of the cell so as to enable induction of its expression, and then inducing expression at the time of viral reconstitution. Further, genomic RNA and viral proteins essential for virus reconstitution are supplied, for example, by transducing the plasmids that express them.

Methods for transducing DNAs expressing the genomic RNAs into cells include the calcium phosphate method (Graham, F. L. and Van Der Eb, J., 1973, Virology 52: 456; Wigler, M. and Silverstein, S., 1977, Cell 11: 223), methods using various transfection reagents, electroporation, or such. The calcium phosphate method can be performed, for example, under the conditions of 2 to 4% $CO_2$, 35° C., 15 to 24 hours, and the DNA concentration in the precipitate mixture of 20 to 30 µg/ml, according to Chen and Okayama (Chen, C. and Okayama, H., 1987, Mol. Cell. Biol. 7: 2745). As a transfection reagent, DEAE-dextran (Sigma #D-9885 M. W. $5\times10^5$), DOTMA(Roche), Superfec™ (QIAGEN #301305), DOTAP, DOPE, DOSPER (Roche #1811169) or the like can be used.

To prevent transfection reagent/DNA complexes from decomposing in endosomes, chloroquine may also be added (Calos, M. P., 1983, Proc. Natl. Acad. Sci. USA 80: 3015). Electroporation has a wide versatility because it is not cell-selective. It is applied by optimizing the duration of pulse electric current, shape of the pulse, potency of electric field (gap between electrodes, voltage), conductivity of buffer, DNA concentration, and cell density.

The methods using transfection reagents are suitable for the transduction into cells of DNA for vector reconstitution, since they are simple to operate and facilitate examination of many samples using a large amount of cells. Preferably, the Superfect™ Transfection Reagent (QIAGEN, Cat No. 301305), or the DOSPER Liposomal Transfection Reagent (Roche, Cat No. 1811169) is used; however, the transfection reagents are not limited to these.

Specifically, virus reconstitution from cDNA can be carried out, for example, as follows:

In a plastic plate of about 6 to 24 wells, or a 100-mm Petri dish or the like, simian kidney-derived LLC-MK2 cells (ATCC CCL-7) are cultured up to about 100% confluency, using minimum essential medium (MEM) including 10% fetal calf serum (FCS) and antibiotics (100 units/ml penicillin G and 100 μg/ml streptomycin). Then they are infected with, for example, two plaque forming units (PFU)/cell of the recombinant vaccinia virus vTF7-3, which expresses T7 RNA polymerase and has been inactivated by 20-minutes of UV irradiation in the presence of 1 μg/ml psoralen (Fuerst, T. R. et al., Proc. Natl. Acad. Sci. USA 83: 8122-8126,1986; Kato, A. et al., Genes Cells 1: 569-579, 1996). The amount of psoralen added and the UV irradiation time can be appropriately adjusted. One hour after infection, 2 to 60 μg, and more preferably 3 to 20 μg, of DNA encoding the genomic RNA of a recombinant Sendai virus is transfected along with the plasmids expressing trans-acting viral proteins essential for viral RNP production (0.5 to 24 μg of pGEM-N, 0.25 to 12 μg of pGEM-P, and 0.5 to 24 μg of pGEM-L) (Kato, A. et al., Genes Cells 1: 569-579, 1996), using the lipofection method or the like with Superfect (QIAGEN). For example, the ratio of the amounts of expression vectors encoding the N, P, and L proteins is preferably 2:1:2, and the plasmid amounts are appropriately adjusted in the range of 1 to 4 μg of pGEM-N, 0.5 to 2 μg of pGEM-P, and 1 to 4 μg of pGEM-L.

The transfected cells are cultured, as desired, in serum-free MEM composed of 100 μg/ml of rifampicin (Sigma) and cytosine arabinoside (AraC), more preferably only 40 μg/ml of cytosine arabinoside (AraC) (Sigma). Optimal drug concentrations are set so as to minimize cytotoxicity due to the vaccinia virus, and to maximize virus recovery rate (Kato, A. et al., 1996, Genes Cells 1: 569-579). After culturing for about 48 to 72 hours after transfection, cells are harvested, and then disintegrated by repeating freeze-thawing three times. LLC-MK2 cells are re-infected with the disintegrated materials including RNP, and cultured. Alternatively, the culture supernatant is recovered, added to a culture solution of LLC-MK2 cells to infect them, and the cells are then cultured. Transfection can be conducted by, for example, forming a complex with lipofectamine, polycationic liposome, or the like, and transducing the complex into cells. Specifically, various transfection reagents can be used. For example, DOTMA (Roche), Superfect™ (QIAGEN #301305), DOTAP, DOPE, and DOSPER (Roche #1811169) may be cited. In order to prevent decomposition in the endosome, chloroquine may also be added (Calos, M. P., 1983, Proc. Natl. Acad. Sci. USA 80: 3015). In cells transduced with RNP, viral gene expression from RNP and RNP replication progress, and the virus is amplified. By diluting the viral solution (culture supernatant) thus obtained (for example, $10^6$-fold), and then repeating the amplification, the vaccinia virus vTF7-3 can be completely eliminated. Amplification is repeated, for example, three or more times. Vectors thus obtained can be stored at −80° C. In order to reconstitute a nontransmissible virus lacking a gene encoding an envelope protein, LLC-MK2 cells expressing the envelope protein may be used for transfection, or a plasmid expressing the envelope protein may be cotransfected. Alternatively, an envelope-gene defective type virus can be amplified by culturing the transfected cells overlaid with LLK-MK2 cells expressing the envelope protein (see WO00/70055 and WO00/70070).

Titers of viruses thus recovered can be determined, for example, by measuring CIU (Cell-Infected Unit) or hemagglutination activity (HA) (WO00/70070; Kato, A. et al., 1996, Genes Cells 1: 569-579; Yonemitsu, Y. & Kaneda, Y., Hemaggulutinating virus of Japan-liposome-mediated gene delivery to vascular cells. Ed. by Baker A H. Molecular Biology of Vascular Diseases. Method in Molecular Medicine: Humana Press: pp. 295-306, 1999). Titers of vectors carrying GFP (green fluorescent protein) marker genes and the like can be quantified by directly counting infected cells, using the marker as an indicator (for example, as GFP-CIU). Titers thus measured can be treated in the same way as CIU (WO00/70070).

So long as a virus can be reconstituted, the host cells used in the reconstitution are not particularly limited. For example, in the reconstitution of Sendai virus vectors and the like, cultured cells such as LLC-MK2 cells and CV-1 cells derived from monkey kidney, BHK cells derived from hamster kidney, and cells derived from humans can be used. By expressing suitable envelope proteins in these cells, infectious virions including the proteins in the envelope can also be obtained. Further, to obtain a large quantity of a Sendai virus vector, a viral vector obtained from an above-described host can be used to infect embrionated hen eggs to amplify the vector. Methods for manufacturing viral vectors using hen eggs have already been developed (Nakanishi, et al., ed. (1993), "State-of-the-Art Technology Protocol in Neuroscience Research III, Molecular Neuron Physiology", Koseisha, Osaka, pp.153-172). Specifically, for example, a fertilized egg is placed in an incubator, and cultured for nine to twelve days at 37 to 38° C. to grow an embryo. After the viral vector is inoculated into the allantoic cavity, the egg is cultured for several days (for example, three days) to proliferate the viral vector. Conditions such as the period of culture may vary depending upon the recombinant Sendai virus being used. Then, allantoic fluids including the vector are recovered. Separation and purification of a Sendai virus vector from allantoic fluids can be performed according to a usual method (Tashiro, M., "Virus Experiment Protocol," Nagai, Ishihama, ed., Medical View Co., Ltd., pp. 68-73, (1995)).

For example, the construction and preparation of Sendai virus vectors defective in F gene can be performed as described below (see WO00/70055 and WO00/70070).

<1>Construction of a genomic cDNA of an F-gene deficient Sendai virus, and a plasmid expressing F gene:

A full-length genomic cDNA of Sendai virus (SeV), the cDNA of pSeV18⁺ b (+) (Hasan, M. K. et al., 1997, J. General Virology 78: 2813-2820) ("pSeV18⁺ b (+)" is also referred to as "pSeV18⁺"), is digested with SphI/KpnI to recover a fragment (14673 bp), which is cloned into pUC18 to prepare plasmid pUC18/KS. Construction of an F gene-deficient site is performed on this pUC18/KS. An F gene deficiency is created by a combination of PCR-ligation methods, and, as a result, the F gene ORF (ATG-TGA=1698 bp) is removed.

Then, for example, atgcatgccggcagatga (SEQ ID NO: 14)' is ligated to construct an F gene-deficient type SeV genomic cDNA (pSeV18⁺/ΔF). A PCR product formed in PCR by using the pair of primers [forward: 5'-gttgagtactgcaagagc/ SEQ ID NO: 15, reverse: 5'-tttgccggcatgcatgtttcccaaggg-gagagttttgcaacc/SEQ ID NO: 16] is connected upstream of F, and a PCR product formed using the pair of primers [forward: 5'-atgcatgccggcagatga/SEQ ID NO: 17, reverse: 5'-tgggtgaat-gagagaatcagc/SEQ ID NO: 18] is connected downstream of the F gene with EcoT22I. The plasmid thus obtained is digested with SacI and SalI to recover a 4931 bp fragment of the region including the F gene-deficient site, which is cloned into pUC18 to form pUC18/dFSS. This pUC18/dFSS is digested with DraIII, the fragment is recovered, replaced with the DraIII fragment of the region comprising the F gene of pSeV18⁺, and ligated to obtain the plasmid pSeV18⁺/ΔF.

A foreign gene is inserted, for example, into the Nsi I and Ngo MIV restriction enzyme sites in the F gene-deficient site ofpUC18/dFSS. For this, a foreign gene fragment may be, for example, amplified using an Nsi I-tailed primer and an Ngo MIV-tailed primer.

<2>Preparation of Helper Cells that Induce SeV-F Protein Expression:

To construct an expression plasmid of the Cre/loxP induction type that expresses the Sendai virus F gene (SeV-F), the SeV-F gene is amplified by PCR, and inserted to the unique Swa I site of the plasmid pCALNdlw (Arai, T. et al., J. Virology 72, 1998, p 1115-1121), which is designed to enable the inducible expression of a gene product by Cre DNA recombinase, thus constructing the plasmid pCALNdLw/F.

To recover infectious virions from the F gene-deficient genome, a helper cell line expressing SeV-F protein is established. The monkey kidney-derived LLC-MK2 cell line, which is commonly used for SeV proliferation, can be used as the cells, for example. LLC-MK2 cells are cultured in MEM supplemented with 10% heat-inactivated fetal bovine serum (FBS), penicillin G sodium (50 units/ml), and streptomycin (50 μg/ml) at 37° C. in 5% $CO_2$. Since the SeV-F gene product is cytotoxic, the above-described plasmid pCALNdLw/F, which was designed to enable inducible expression of the F gene product with Cre DNA recombinase, is transfected to LLC-MK2 cells by the calcium phosphate method (using a mammalian transfection kit (Stratagene)), according to protocols well known in the art.

The plasmid pCALNdLw/F (10 μg) is transduced into LLC-MK2 cells grown to 40% confluency using a 10-cm plate, and the cells are then cultured in MEM (10 ml) including 10% FBS, in a 5% $CO_2$ incubator at 37° C. for 24 hours. After 24 hours, the cells are detached and suspended in the medium (10 ml). The suspension is then seeded into five 10-cm dishes, 5 ml into one dish, 2 ml each into two dishes, and 0.2 ml each into two dishes, and cultured in MEM (10 ml) including G418 (GIBCO-BRL) (1200 μg/ml) and 10% FBS. The cells were cultured for 14 days, exchanging the medium every two days, to select cell lines stably transduced with the gene. The cells grown from the above medium that show G418 resistance are recovered using a cloning ring. Culture of each clone thus recovered is continued in 10-cm plates until confluent.

After the cells have grown to confluency in a 6-cm dish, F protein expression can be induced by infecting the cells with adenovirus AxCANCre, for example, at MOI=3, according to the method of Saito, et al. (Saito et al., Nucl. Acids Res. 23: 3816-3821 (1995); Arai, T. et al., J. Virol 72, 1115-1121 (1998)).

<3>Reconstruction and Amplification of F Gene-Deficient SeV Virus:

The above-described plasmid pSeV18⁺/ΔF inserted with the foreign gene is transfected into LLC-MK2 cells by the procedure described below. LLC-MK2 cells are seeded on 100-mm dishes at $5 \times 10^6$ cells/dish. To transcribe the genomic RNA using T7 RNA polymerase, the cells are cultured for 24 hours, and then recombinant vaccinia virus, which expresses T7 RNA polymerase (PLWUV-VacT7: Fuerst, T. R. et al., Proc. Natl. Acad. Sci. USA 83, 8122-8126 (1986)) and is treated with psoralen and long-wavelength ultraviolet light (365 nm) for 20 minutes, is inoculated to the cells at a MOI of about 2 at room temperature for one hour. The ultraviolet light irradiation to the vaccinia virus can be achieved, for example, by using UV Stratalinker 2400 with five 15-watt bulbs (Catalog No. 400676 (100V); Stratagene, La Jolla, Calif., USA). After the cells are washed with serum-free MEM, plasmid expressing the genomic RNA and expression plasmids each expressing N, P, L, F, or HN protein of the minus-strand RNA virus are transfected into the cells using an appropriate lipofection reagent. The plasmid ratio is preferably, but is not limited to, 6:2:1:2:2:2 in this order. For example, the expression plasmid for the genomic RNA, and the expression plasmids each of which expresses N, P, or L protein, or F and HN proteins (pGEM/NP, pGEM/P, pGEM/L, and PGEM/F-HN; WO00/70070, Kato, A. et al., Genes Cells 1, 569-579 (1996)) are transfected at amounts of 12, 4, 2, 4, and 4 μg/dish, respectively. After a few hours of culture, the cells are washed twice with serum-free MEM, and then cultured in MEM supplemented with 40 μg/ml cytosine β-D-arabinofuranoside (AraC: Sigma, St. Louis, Mo.) and 7.5 μg/ml trypsin (Gibco-BRL, Rockville, Md.). The cells are recovered, and the resulting pellet is suspended in OptiMEM ($10^7$ cells/ml). The suspension is subjected to three freeze-thaw cycles, and mixed with lipofection reagent DOSPER (Roche #1811169) ($10^6$ cells/25 μl DOSPER). After the mixture is allowed to stand at room temperature for 15 minutes, it is transfected to F-expressing helper cells ($10^6$ cells/well in 12-well-plate) cloned as described above. The cells are cultured in serum-free MEM (containing 40 μg/ml AraC and 7.5 μg/ml trypsin), and the supernatant is collected. Viruses deficient in genes other than F, for example, HN and M genes, can be prepared by a similar method as described above.

F gene or HN gene deletion is effective for rendering SeV vectors nontransmissible, while M gene deletion is effective for disabling formation of virions from infected cells. Vectors that are deleted of an arbitrary combination of at least two of the F, HN, and M genes are safer. For example, SeV lacking both M and F genes (SeV/ΔMΔF) is a vector that is nontransmissible and lacks the ability to form virions. SeV/ΔMΔF retains high infectivity and high gene-expressing ability in vitro and in vivo, equivalent to those of the wild type SeV vector. These characteristics of SeV/ΔMΔF may further contribute to the improved safety of SeV in anti-tumor treatment.

For the preparation of viral gene-deficient vectors, for example, two or more types of vectors which differ in the deficient viral gene on the viral genome carried by the vector are introduced into same cells. The respective deficient viral proteins are supplied through the expression from the other vector(s). Therefore, the vectors complement each other to form infectious viral particles, resulting in a complete replication cycle and amplification of the viral vectors. Specifically, when two or more types of viral vectors of the present invention are inoculated in combination that allows complementation of viral proteins, a mixture of the viral gene-deficient vectors can be produced on a large scale at low cost. Since such viruses lack viral genes, their genome sizes are smaller than those of viral gene-nondeficient viruses and thus can carry larger foreign genes. Furthermore, these viruses that are non-proliferative due to the lack of viral genes become diluted outside cells, which makes it difficult to maintain their coinfection. The viruses become sterile and thus are advantageous from the viewpoint of controlling their environmental release.

According to the method for producing viruses as described herein, the viral vector of the present invention can be released into extracellular fluid of virus producing cells at a titer of, for example, $1\times10^5$ CIU/ml or higher, preferably $1\times10^6$ CIU/ml or higher, more preferably $5\times10^6$ CIU/ml or higher, more preferably $1\times10^7$ CIU/ml or higher, more preferably $5\times10^7$ Ciru/ml or higher, more preferably $1\times10^8$ CIU/ml or higher, and more preferably $5\times10^8$ CIU/ml or higher. The titer of virus can be determined according to methods described herein or elsewhere (Kiyotani, K. et al., Virology 177(1), 65-74 (1990); and WO00/70070).

The recovered viral vectors can be purified to be substantial pure. The purification can be achieved using known purification/separation methods, including filtration, centrifugation, adsorption, and column purification, or any combinations thereof. The phrase "substantially pure" means that the virus component constitutes a major proportion of a solution of the viral vector. For example, a viral vector composition can be confirmed to be substantially pure by the fact that the proportion of protein contained as the viral vector component to the total protein (excluding proteins added as carriers and stabilizers) in the solution is 10% (w/w) or greater, preferably 20% or greater, more preferably 50% or greater, preferably 70% or greater, more preferably 80% or greater, and even more preferably 90% or greater. Specific purification methods for, for example, the paramyxovirus vector includes methods using cellulose sulfate ester or cross-linked polysaccharide sulfate ester (Japanese Patent Application Kokoku Publication No. (JP-B) S62-30752 (examined, approved Japanese patent application published for opposition), JP-B S62-33879, and JP-B S62-30753) and methods including adsorbing to fucose sulfate-containing polysaccharide and/or degradation products thereof (WO97/32010), but are not limited thereto.

In the production of compositions containing the viral vector of the present invention, the vector may be combined with desired pharmaceutically acceptable carriers or media according to needs. The "pharmaceutically acceptable carriers or media" refers to materials that can be administered together with the vector and that do not significantly inhibit the gene transfer via the vector. Such carriers and media include, for example, sterile water, sodium chloride solution, dextrose solution, Ringer's solution containing dextrose, sodium chloride, and lactate, culture medium, serum, and phosphate buffered saline (PBS). They may be appropriately combined with the vector to formulate a composition. The composition of the present invention may include carriers or media such as deionized water and aqueous dextrose solution. The composition may also include membrane stabilizers for liposome (for example, sterols such as cholesterol). The composition may also include antioxidants (for example, tocopherol or vitamin E). In addition, the composition may also include vegetable oils, suspending agents, detergents, stabilizers, biocidal agents, and the like. Furthermore, preservatives and other additives may also be added. The formula of the present composition may be aqueous solution, capsule, suspension, syrup, or the like. The composition of the present invention may also be in a form of solution, freeze-dried product, or aerosol. When it is a freeze-dried product, it may include sorbitol, sucrose, amino acids, various proteins, and the like as a stabilizer. The present invention is related to anti-tumor agents containing a minus-strand RNA viral vector that encodes an immunostimulatory cytokine. The invention is also related to anti-tumor agents containing cells introduced with a minus-strand RNA viral vector that encodes an immunostimulatory cytokine. Compositions containing the vector of the present invention and cells introduced with the vector are useful as anti-tumor pharmaceuticals. Furthermore, the vector compositions of the present invention and the cells introduced with the vector are also useful as anti-tumor vaccines. The vector compositions and the cells may include immunostimulants such as cytokine, cholera toxin, and Salmonella toxin to improve immunogenicity. Furthermore, the vaccine may be combined with adjuvants, such as alum, incomplete Freund's adjuvant, MF59 (oil emulsion), MTP-PE (muramyl tripeptide derived from cell wall of mycobacteria), and QS-21 (derived from soapbark tree *Quilaja saponaria*).

When administering the composition or cell, it is effective to combine them with cytokines that improve the adjuvant effect. Such genes include, for example,
  (i) single-chain IL-12 (Proc. Natl. Acad. Sci. USA 96 (15): 8591-8596, 1999);
  (ii) interferon-y (U.S. Patent No. 5,798,100);
  (iii) granulocyte colony stimulating factor (GM-CSF); and
  (iv) a combination of GM-CSF and IL-4 (J. Neurosurgery 90 (6), 1115-1124 (1999)).

The dose of a minus-strand RNA viral vector may vary depending upon the disorder, body weight, age, gender, and symptoms of patients, as well as the form of the composition to be administered, administration method, cytokine gene to be transduced, and so on; however, those skilled in the art can appropriately determine the dosage. Administration route can be appropriately selected; for example, the vector is injected into a tumor by injector or catheter. Doses of the virus are preferably administered in a pharmaceutically acceptable carrier in a range of preferably about $10^5$ CIU/ml to about $10^{11}$ CIU/ml, more preferably about $10^7$ CIU/ml to about $10^9$ CIU/ml, most preferably about $1\times10^8$ CIU/mi to about $5\times10^8$ CIU/ml. In humans, a single dose is preferably in the range of $2\times10^5$ CIU to $2\times10^{11}$ CIU, and can be administered once or more, so long as the side effects are within a clinically acceptable range. The same applies to the number of administrations per day. With non-human animals, for example, the above-described doses can be converted based on the body weight ratio or volume ratio of a target site for administration (e.g. average values) between the animal of interest and human, and the converted doses can be administered to the animal. After administering a transmissible minus-strand RNA viral vector to an individual or cell, when the proliferation of the viral vector must be restrained upon treatment completion and such, it is also possible to specifically restrain only the proliferation of the viral vector, with no damage to the host, by administering an RNA-dependent RNA polymerase inhibitor. For ex vivo administration, a vector is contacted with target cells outside the body (for example, in a test tube or dish). The vector is preferably administered at an MOI of 1 to 500, more preferably 2 to 300, still more preferably 3 to 200, yet preferably 5 to 100, even more preferably 7 to 70.

The administration of a minus-strand RNA viral vector encoding an immunostimulatory cytokine, or cells into which the vector has been introduced, into tumor sites is preferably combined with immunization with a tumor antigen or a vector expressing the antigen. As shown in the Examples, a treatment combining in-vivo administration of the vector of the present invention and immunization with a tumor antigen produces significantly strong anti-tumor effect as compared to administration of the vector alone. The inoculation of the tumor antigen or the vector expressing the antigen may be carried out simultaneously or before or after administration of the immunostimulatory cytokine-encoding minus-strand RNA viral vector. The interval between administration of the immunostimulatory cytokine-encoding minus-strand RNA viral vector and inoculation of a tumor antigen or a vector expressing the antigen is, for example, 7 days or less, preferably 6 days or less, 5 days or less, 4 days or less, 3 days or less, or 2 days or less, more preferably 24 hours or less. The tumor antigen used for the immunization includes, for example, tumor cells that have lost their growth ability, and tumor cell lysates. It is preferable to eliminate the growth ability of tumor cells by heating, radiation, mitomycin C treatment, or such. For example, when X-ray irradiation is used, a total radiation dose of 700 to 3300 Rad can be irradiated. The mitomycin C treatment can be carried out, for example, by adding 25 to 50 μg/ml mitomycin C to cells and incubating the cells at 37° C. for 30 to 60 minutes. The heat treatment of cells can be achieved, for example, by heating at 50 to 65° C. for 20 minutes. Alternatively, instead of tumor cells, tumor antigens expressed in target tumor cells may be used. Such tumor antigens may be naturally occurring or recombinant polypeptides. Alternatively, a tumor antigen-expressing vector can be administered. The tumor antigen-expressing vector is not particularly limited; for example, desired expression vectors that have the ability to express a tumor antigen in administered subjects, such as plasmid, viral vector, and naked DNA, are used. Such vectors may be those containing a nucleic acid in which a nucleic acid encoding a tumor antigen is linked downstream of an appropriate promoter (for example, SV40 promoter, CAG promoter, CMV promoter, EF1 promoter, or LTR promoter). Alternatively, when viral vectors are used, a tumor antigen-encoding nucleic acid is linked so that its expression is controlled under an expression regulatory sequence suitable for each viral vector. The vector may be administered in vivo or ex vivo. The tumor antigen is appropriately selected depending on the type of cancer to be treated. Such tumor antigens include, for example, Muc-1 or Muc-1-like mucin tandem repeat peptide (U.S. Patent No.5, 744,144) involved in ovarian cancer and such; E6 and E7 proteins of human papilloma virus which causes cervical cancer; melanoma antigens MART-1, MAGE-1, -2, and -3, gp100 and tyrosinase; prostate cancer antigen PSA; as well as CEA (Kim, C. et al., Cancer Immunol. Immunother. 47 (1998) 90-96); and Her2neu (HER2p 63-71, p 780-788; Eur. J. Immunol.2000; 30: 3338-3346). Sites for inoculating tumor antigens are selected appropriately. The inoculation can be achieved, for example, percutaneously, intranasally, intrabronchially, intramuscularly, intraperitoneally, intravenously, or subcutaneously. The antigen is preferably inoculated subcutaneously. When tumor cells or lysates thereof are inoculated, the dose may be generally $10^5$ to $10^9$ cells, preferably $10^6$ to $10^8$ cells, more preferably about $10^7$ cells. The present invention also relates to kits for anti-tumor treatment, which comprise minus-strand RNA viral vectors encoding immunostimulatory cytokines, and tumor antigens or vectors expressing the antigens. The kits are packages containing immunostimulatory cytokine-encoding minus-strand RNA viral vectors and tumor antigens or vectors expressing the antigens. The packages comprise, for example, vessels containing the minus-strand RNA viral vectors and vessels containing the tumor antigens or vectors expressing the antigens. Such packages are used to carry out the combinatory treatment described herein.

The anti-tumor treatment method of the present invention can be used for any solid tumors. The method is particularly suitable for treating tumors in tissues of the central nervous system (including brain intraparenchymal or extraparenchymal tissue), for example, brain tumors such as glioma, metastatic brain tumors, medulloblastoma, germ cell tumors, meningioma, pituitary adenoma, and neurilemoma. The method is particularly preferably used to treat glioma. Immunostimulatory cytokine-encoding minus-strand RNA viral vectors have the ability to deliver cytokine genes to brain tumors with high efficiency, and induce significant migration of immune cells that are activated in peripheral tissues into brain tumor tissues. In addition, when used in combination with tumor antigen immunization, the vectors can suppress the growth of brain tumors. For introducing a vector into the central nervous system, see the following references: Bitzer, M. et al. J. Gene Med. 5:543-553, 2003; Li, H.O. et al., J. Virol. 74: 6564-6569, 2000; Inoue, M. et al., Mol. Ther. 5:S174, 2002; Shirakura, M. et al., Exp. Animal 52: 119-127, 2003; Suzuki, S. et al., Eur. J. Neurosci. 13: 2299-2308, 2001.

Species that are subjected to the anti-tumor treatment of the present invention are not particularly limited, but comprise desired mammals including human and nonhuman mammals, specifically, human, mouse, rat, dog, pig, cat, bovine, rabbit, sheep, goat, and monkey.

EXAMPLES

Herein below, the present invention will be specifically described using Examples, however, it is not to be construed as being limited thereto. All references cited herein are incorporated as parts of the present specification.

Cells and Animals

Rat 9L gliosarcoma cells were maintained in Dulbecco's modified Eagle medium containing 10% FCS under wet atmosphere containing 5% $CO_2$. Male Fisher 344 rats with weights of 200 and 240 g (7 to 8 weeks old) were used in the experiments described below. These animals were maintained under a specific pathogen-free (SPC) environment according to the Laboratory Animal Resources Commission Standards.

Brain Tumor Model and Therapy

Animals were anesthetized and fixed in a stereotaxic apparatus. A burr hole was created at an appropriate position (4 mm posterior to the bregma, 3 mm right from the midline). A 25-gauge needle was inserted at a position 3 mm ventral to the dura. 10 μl medium containing $10^5$ syngenic 9L tumor cells was slowly (over a period of 5 minutes) injected using a microinjector (Harvard Apparatus, South Natick, Mass.) (day 0). The therapeutic step began 3 days after the intracerebral (i.c.) inoculation of 9L tumor cells (day 3). The animals were subjected to i.c. transplantation of SeV18$^+$ hIL2/ΔMΔF or SeV18$^+$lacZ/ΔMΔF and/or subcutaneous (s.c.) immunization with irradiated wild type 9L tumor cells. The i.c. administration was achieved by administering 1×$10^7$ CIU of each SeV in 10 μl PBS at the same stereotaxic coordinates as described above. For the s.c. immunization, 100 μl medium containing 1×$10^6$ wild type 9L cells irradiated with 30 Gy was inoculated into the lower abdominal quadrant (Iwadate, Y et al., Cancer Res., 61: 8769-8774, 2001).

MRI and Viability Test

All animals inoculated with tumor cells were examined by MRI every 7 days to evaluate the volumes of i.c. tumors. 0.2 ml of Gd-DTPA (0.8-1.0 ml/kg) was injected into rats anesthetized with 50 mg/kg pentobarbital. T1-weighted images of coronal sections (TR 500 msec; TE 11 msec; 3 mm thickness; gapless) were obtained using a 1.5 Tesla MR system (Sigma Advantage, General Electric, Milwaukee, Wis.). The tumor volume (mm³) was calculated as a sum of Gd-DTPA enhanced areas in each MR image area (mm²) multiplied by its image thickness. The tumor volume estimated by MRI is linearly correlated with the actual tumor weight measured immediately after image analysis (Namba, H. et al., Human Gene Ther., 7: 1847-1852, 1996). The tumor volume in each group was analyzed by univariate analysis of variance (one-factor ANOVA)).

Rats were observed every day until they showed severe paresis, ataxia, periophthalmic encrustations, or more than 20% weight loss. Since the life expectancy of such animals is less than 1 day, the day of sacrifice is regarded as the "death date". The viability analysis was conducted using the log-rank test, based on the Kaplan-Meier method.

Immunohistochemistry

Tumor-bearing rats were perfused through the ascending aorta with 4% paraformaldehyde. Brains were removed from the rats. 15-µm frozen sections from the brain samples were reacted with anti-CD4 (W3/25, Serotec, Oxford, UK), anti-CD8(OX-8, Serotec), anti-NK cell (1.2.3, Serotec), and anti-human IL-2 (DAKO, Tokyo, Japan) monoclonal antibodies, and then reacted with a horseradish peroxidase-conjugated goat anti-mouse IgG (MBL, Nagoya, Japan). Then, the sections were stained with 3, 3'-diaminobenzidine tetrahydrochloride (Sigma, St. Louis, Mo.). The expression of β-galactosidase was detected by histochemical staining with X-Gal.

Example 1

Construction of a Recombinant Minus-Strand RNA Viral Vector Carrying Human IL-2 Gene In the full-length Sendai virus (SeV) genome, viral genes are arranged in the following order: the 3' leader (ld), viral genes of nucleocapsid (NP), phospho (P), matrix (M), fusion (F), hemagglutinin neuraminidase (HN), and large (L), and the last 5' short trailer (tr) (FIG. 1). An SeV vector lacking both the M and F genes (SeV/ΔMΔF) was used in the experiments. Since the F protein is essential for viral infection and the M protein functions in the assembly and budding of viruses, SeV/ΔMΔF is nontransmissible and does not form virions from infected cells. SeV/ΔMΔF vector carrying a human IL-2 gene (hIL-2-SeV/ΔMΔF) and SeV/ΔMΔF vector carrying a lacZ gene (lacZ-SeV/ΔMΔF) were constructed as previously described (Inoue, M. et al., J. Virol., 77: 6419-6429, 2003; Inoue, M. et al., Mol. Ther., 5: S174, 2002). Specifically, the human IL-2 cDNA (Accession number: A14844) was amplified using a pair of NotI tagged primers containing an SeV-specific transcriptional regulatory signal sequence: 5'—ACTTGCGGCCGCGTTTAAACG-GCGCGCCATGTACAGGATGCAACTCCTGTC-3' (SEQ ID NO: 19) and 5'—ATCCGCGGCCGCGAT-GAACTTTCACCCTAAGTTTTTCTTAC-TACGGATTTAAATG GCGCGCCA-3' (SEQ ID NO: 20). The amplified fragment was inserted into the NotI site of the original pSeV18⁺/ΔMΔF. The hIL-2-SeV/ΔMΔF cDNA (phIL2-SeV/ΔMΔF) was thus constructed. The lacZ-SeV/ΔMΔF cDNA (placZ-SeV/ΔMΔF) was constructed using an amplified lacZ fragment (Li, H. O. et al., J. Virol., 74: 6564-6569, 2000) by the same procedure. LLC-MK2 cells were infected with the vaccinia virus vTF7-3 (Fuerst, T. R. et al., Proc. Natl. Acad. Sci. USA, 83: 8122-8126, 1986) which expresses the T7 RNA polymerase, and then transfected with phIL2-SeV/ΔMΔF or placZ-SeV/ΔMΔF. The RNA genomes of hIL2-SeV/ΔMΔF and lacZ-SeV/ΔMΔF, whose transcription was driven by the T7 RNA polymerase, were encapsulated with the N, P and L proteins whose expression was driven by each of the co-transfected plasmids (Ikeda, Y et al., Exp. Eye Res., 75: 39-48, 2002). The SeV vectors that were harvested were amplified using a packaging cell line expressing both the M and F proteins (Inoue, M. et al., J. Virol., 77: 6419-6429, 2003; Inoue, M. et al., Mol. Ther., 5: S174, 2002). The virus titer was determined based on the infectivity and is presented in cell infectious units (CIU). The SeV vectors were stored at −80° C. prior to use.

Example 2

Intracerebral Introduction of β-galactosidase Gene with the SeV Vector

Efficiency of intracerebral introduction of β-galactosidase gene using the SeV vector was examined in normal brain tissues and brain tumors, which were removed 4, 7, and 14 days after the injection of lacZ-SeV/ΔMΔF (also abbreviated as SeV/LacZ). When the vector was injected into brain tumor tissues, the appearance of the vector-injected tissues typically showed dispersed colonies of X-gal-positive cells, consisting of the lacZ-SeV/ΔMΔF-injected tumor cells and progenitor cells thereof (FIG. 2). Tumor cells that were not introduced with the vector were detected between dispersed X-gal-stained colonies. The expression or accumulation of β-galactosidase reached the maximal level 7 days after the vector injection, and the expression level was maintained on day 14 (FIG. 2). The vector introduction was hardly observed in normal brain tissues surrounding the tumor, except in choroid plexus. When injected into normal brain tissues, the vector was found to be introduced into neurons and glial cells with a similar efficiency as in the intratumoral injection. Ependymal cells were not introduced when the vector was injected intraparenchymally.

Example 3

Anti-tumor Effect of the i.c. Injection of the hIL2-SeV/ΔMΔF Vector

Figure 3:
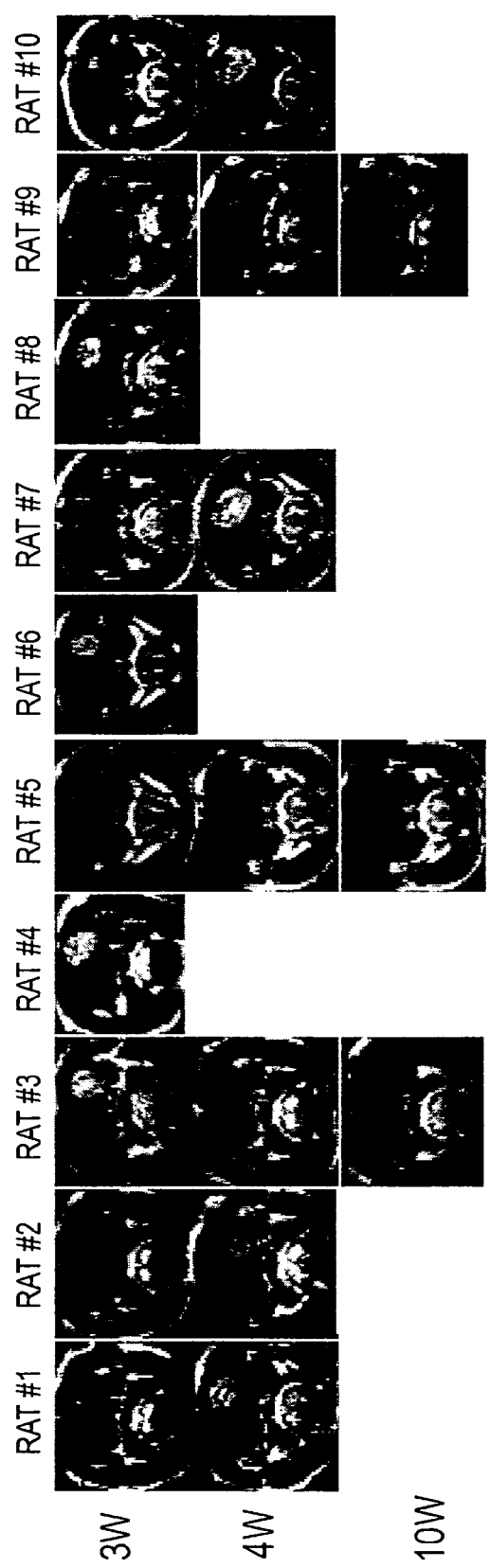
FIG. 3 shows MRI images of the whole 9L brain tumor treated with intracerebral administration of hIL2-SeV/ΔMΔF and subcutaneous immunization with irradiated 9L cells (T1-weighted image of a coronal plane after Gd-DTPA injection). The tumor in the Gd-DTPA enhanced T1-weighted image is visualized as a white region. In three of the ten rats tested, established brain tumors, which were detected three weeks after inoculation of tumor cells, were completely eliminated by week 4 with the combination therapy (Rat #3, Rat #5, and Rat #10).
Figure 4:
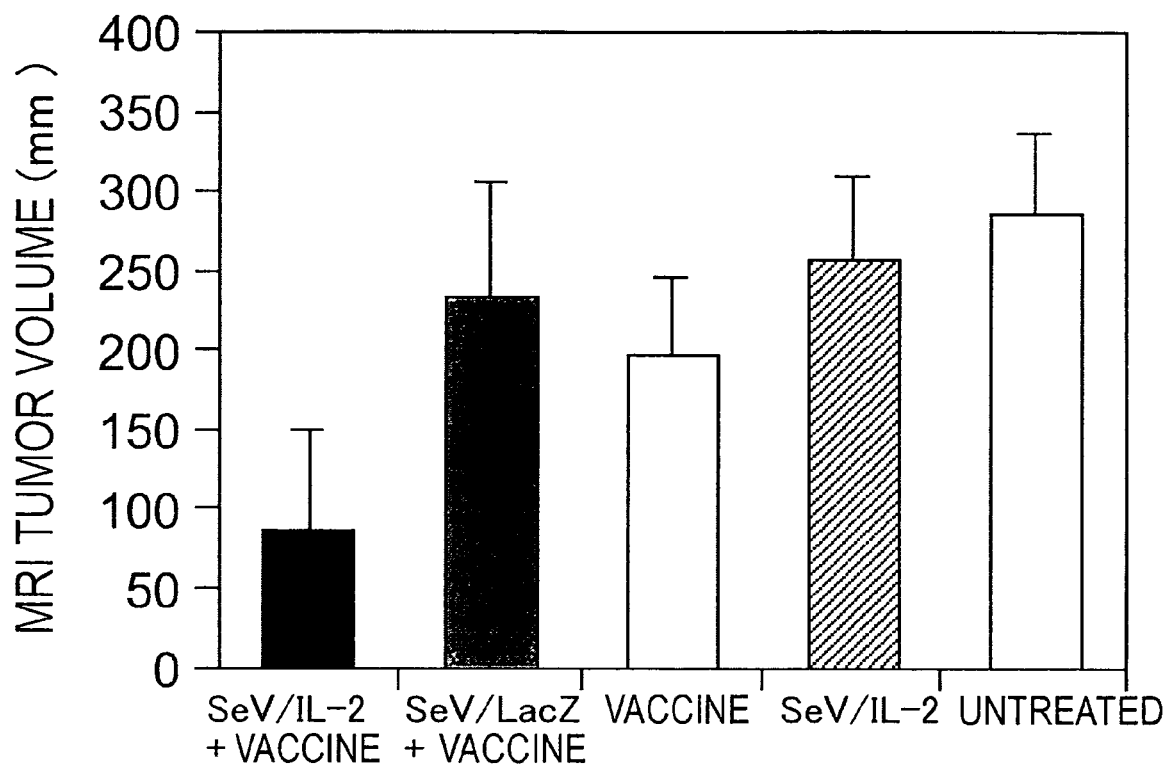
FIG. 4 shows an evaluation of the mean volume of 9L brain tumors based on Gd-DTPA-enhanced MRI three weeks after the inoculation of tumor cells. A combination of the administration of hIL2-SeV/ΔMΔF and subcutaneous immunization significantly reduced the volume ($86.5 \pm 63.8$ mm$^3$, n=10) as compared with no treatment ($286 \pm 51.2$ mm$^3$, n=10), the subcutaneous immunization alone ($197 \pm 48.9$ mm$^3$, n=10), intracerebral administration of lacZ-SeV/ΔMΔF in combination with subcutaneous immunization ($233 \pm 73.2$ mm$^3$, n=6), or intracerebral administration of hIL2-SeV/ΔMΔF alone ($256 \pm 53.2$ mm$^3$, n=6). Each bar represents a "mean±S. E.".
Figure 5:
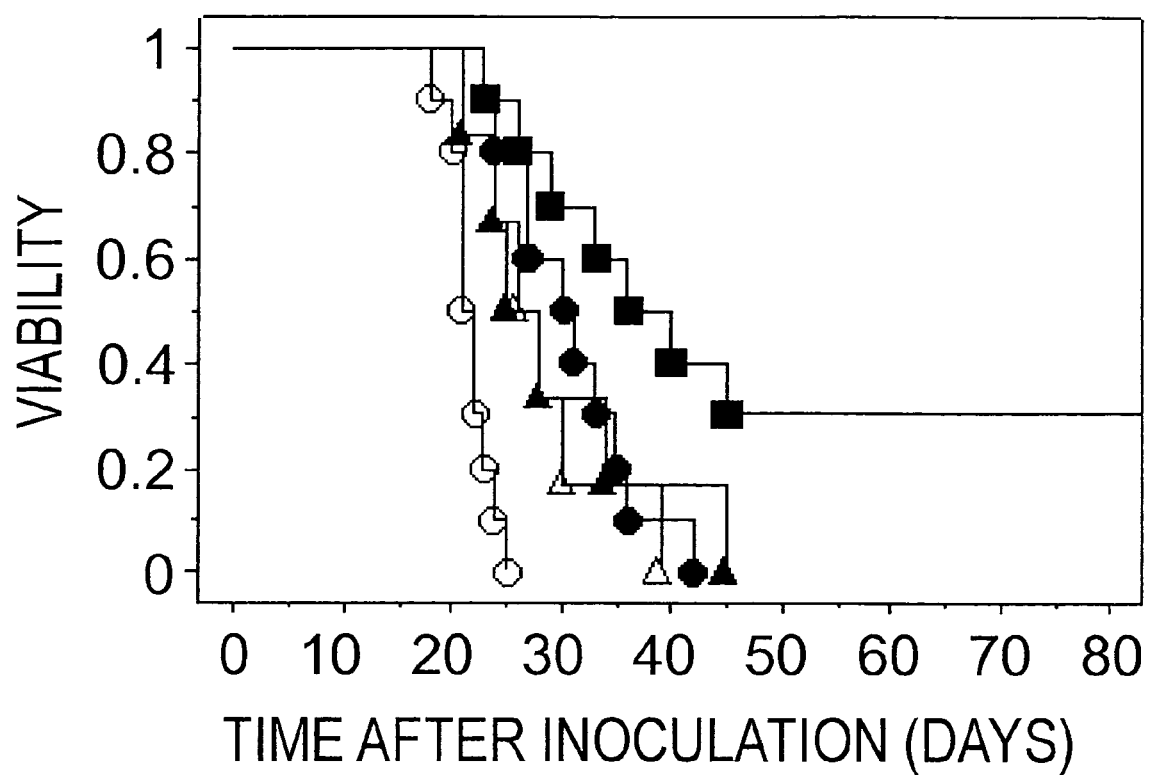
FIG. 5 shows Kaplan-Meier survival curves for rats that were intracerebrally inoculated with 9L cells on day 0, and subjected to vector administration and/or immunization with irradiated tumor cells on day 3. Untreated control (open circle); subcutaneous immunization alone (closed circle); intracerebral administration of lacZ-SeV/ΔMΔF and subcutaneous immunization (closed triangle); intracerebral administration of hIL2-SeV/ΔMΔF alone (open triangle); intracerebral administration of hIL2-SeV/ΔMΔF in combination with subcutaneous immunization (closed square). Statistical analyses based on a log-rank test demonstrated that rats treated with intracerebral administration of hIL2-SeV/ΔMΔF and subcutaneous immunization survived significantly longer than the other treated groups ($p<0.05$).

Naïve rats intracerebrally inoculated with 9L gliosarcoma developed progressive tumors, and all of them died by the 25th day after inoculation (day 25). The therapeutic effect of the i.c. injection of hIL2-SeV/ΔMΔF (abbreviated as SeV/IL-2) in combination with a subcutaneous (s.c.) immunization using an irradiated whole-tumor-cell vaccine was examined by determining the tumor volume using serial Gd-enhanced MRI (FIG. 3). After three weeks (day21) of 9L tumor cell inoculation, the tumor volume (86.5±63.8 mm³, n=10, on day 21) of the rats subjected to intracerebral administration of hIL2-SeV/ΔMΔF and s.c. immunization was found to be significantly reduced as compared with the untreated rats (286±51.2 mm³, n=10, on day 21), rats subjected to s.c. immunization alone (197±48.9 mm³, n=10, on day 21), i.c. administration of lacZ-SeV/ΔMΔF in combination with s.c. immunization (233±73.2 mm³, n=6, on day 21), or i.c. administration of hIL2-SeV/ΔMΔF alone (256±53.2 mm³, n=6, on day 21) (FIG. 4). The combinatory treatment using hIL2-SeV/ΔMΔF completely eliminated established brain tumors in three of the ten rats by day 21 (FIG. 3). In contrast, i.c. administration of hIL2-SeV/ΔMΔF alone or s.c. immunization alone reduced the mean tumor volume when compared with the untreated rats, but their therapeutic effect was weaker than that of the combinatory treatment, and thus, a complete elimination of the established tumors was not observed (FIG. 4). As shown in FIG. 5, although when compared with the untreated rats, the life time of the tumor-bearing rats was prolonged by i.c. administration of hIL2-SeV/ΔMΔF alone or s.c. immunization alone, the life time of the rats subjected to i.c. administration of hIL2-SeV/ΔMΔF vector in combination with s.c. immunization was significantly prolonged when compared with the untreated control rats or rats subjected to the other treatments (p<0.05, Logrank test) (FIG. 5). When hIL2-SeV/ΔMΔF was injected into the hemisphere opposite to the established tumor, the tumor growth was not affected (data not presented). This result suggests that IL-2 needs to be expressed adjacently to the target tumor in order to produce a marked therapeutic effect.

Example 4

Immunohistochemical Analysis

Figure 6:
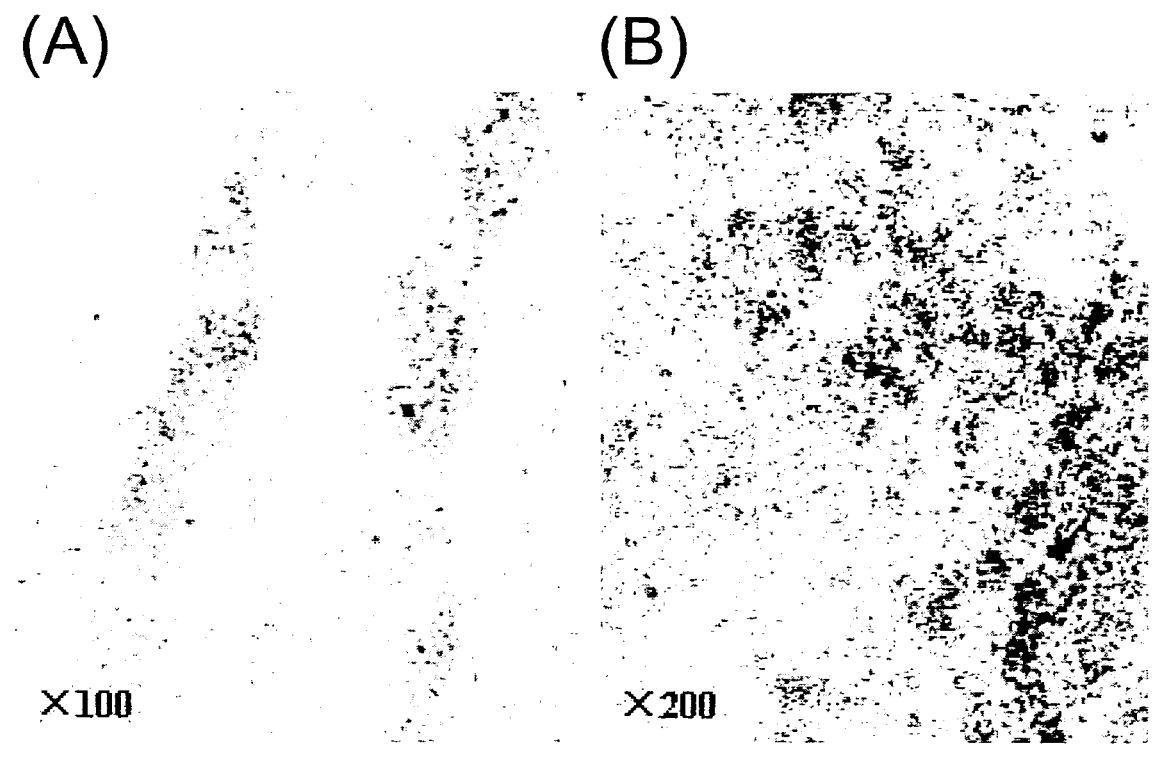
Figure 7:
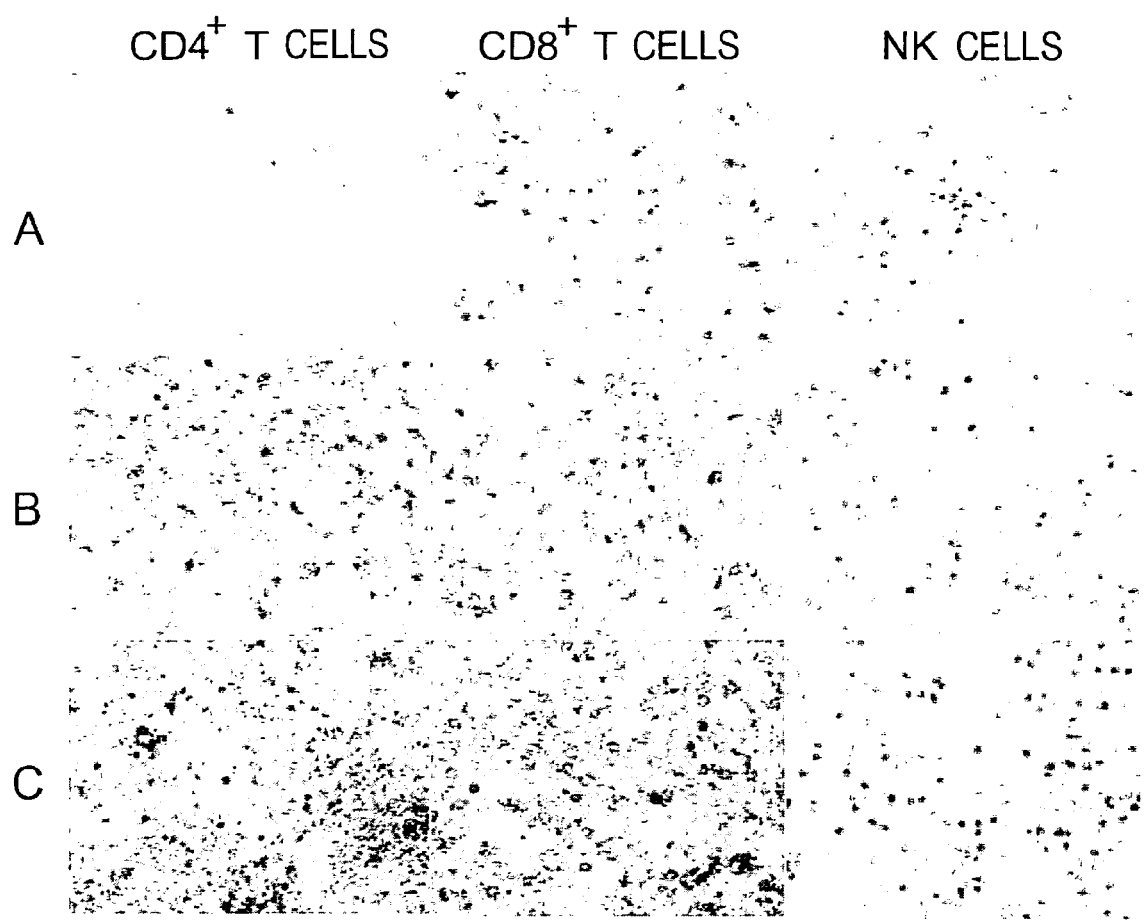
FIG. 7 shows immunohistochemical analyses of the expression of CD4, CD8, and NK cell antigens in rats treated with intracerebral administration of lacZ-SeV/ΔMΔF and subcutaneous immunization with irradiated 9L cells (A), intracerebral administration of hIL2-SeV/ΔMΔF alone (B), and intracerebral administration of hIL2-SeV/ΔMΔF in combination with subcutaneous immunization (C). (Magnification: ×200). The infiltration of CD4$^+$ T cells and CD8$^+$ T cells was more significantly detected in tumors treated with intracerebral administration of hIL2-SeV/ΔMΔF vector and subcu-

The expression of IL-2 protein in brain tumors was examined by immunohistochemistry. The IL-2 protein was observed to be dispersedly expressed in tumors injected with the hIL2-SeV/ΔMΔF vector (FIG. 6). Furthermore, the presence of CD4$^+$T cells, CD8$^+$T cells, and NK cells was investigated. Marked infiltration of CD4$^+$T cells, CD8$^+$T cells, and NK cells was detected in tumors that were subjected to i.c. administration of hIL2-SeV/ΔMΔF vector and s.c. immunization (FIG. 7). The migration of these cells was moderately detected in tumors treated with i.c. injection of the lacZ-SeV/ΔMΔF vector and s.c. immunization, or i.c. administration of the hIL2-SeV/ΔMΔF vector alone; however, the combinatory treatment resulted in a more marked cell migration than the single treatments.

INDUSTRIAL APPLICABILITY

The present invention provides a new therapeutic method for tumors. The method of the present invention is expected to be widely applicable to cancer therapy because it can suppress tumor growth effectively with a simple procedure.

The invention claimed is:

1. A method of anti-tumor treatment comprising the step of intracerebrally administering to a subject having a brain tumor, an effective amount of a Sendai virus vector which encodes interleukin-2 or a cell into which the vector has been introduced.

2. The method of claim 1, wherein the Sendai virus vector lacks both M and F genes.

3. The method of claim 1 further comprising the step of subcutaneously administering tumor cells from the brain tumor, wherein the tumor cells have lost their growth ability.

4. The method of claim 3, wherein the Sendai virus vector lacks both M and F genes.

* * * * *